United States Patent
Betageri et al.

(10) Patent No.: US 9,844,557 B2
(45) Date of Patent: *Dec. 19, 2017

(54) PROLIPOSOMAL TESTOSTERONE FORMULATIONS

(71) Applicants: WESTERN UNIVERSITY OF HEALTH SCIENCES, Pomona, CA (US); TESORX PHARMA, LLC, Pomona, CA (US)

(72) Inventors: Guru V. Betageri, Chino Hills, CA (US); Ramachandran Thirucote, Atherton, CA (US); Veeran Gowda Kadajji, North Hollywood, CA (US)

(73) Assignees: WESTERN UNIVERSITY OF HEALTH SCIENCES, Pomona, CA (US); TESORX PHARMA, LLC, Pomona, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/268,917

(22) Filed: Sep. 19, 2016

(65) Prior Publication Data

US 2017/0065614 A1 Mar. 9, 2017

Related U.S. Application Data

(63) Continuation of application No. 15/250,169, filed on Aug. 29, 2016, now Pat. No. 9,623,033, which is a continuation of application No. 14/604,985, filed on Jan. 26, 2015, now Pat. No. 9,445,995, which is a continuation of application No. 14/149,227, filed on Jan. 7, 2014, now Pat. No. 8,957,053, which is a continuation of application No. PCT/US2013/040325, filed on May 9, 2013.

(60) Provisional application No. 61/664,996, filed on May 9, 2012.

(51) Int. Cl.

| | | |
|---|---|---|
| *A61K 31/568* | (2006.01) | |
| *A61K 9/127* | (2006.01) | |
| *A61K 31/575* | (2006.01) | |
| *A61K 9/10* | (2006.01) | |
| *A61K 9/14* | (2006.01) | |
| *A61K 9/19* | (2006.01) | |
| *A61K 9/20* | (2006.01) | |
| *A61K 9/48* | (2006.01) | |
| *A61K 9/28* | (2006.01) | |
| *A61K 9/00* | (2006.01) | |

(52) U.S. Cl.
CPC .......... *A61K 31/568* (2013.01); *A61K 9/0053* (2013.01); *A61K 9/10* (2013.01); *A61K 9/127* (2013.01); *A61K 9/1277* (2013.01); *A61K 9/145* (2013.01); *A61K 9/19* (2013.01); *A61K 9/2013* (2013.01); *A61K 9/2846* (2013.01); *A61K 9/4858* (2013.01); *A61K 9/4866* (2013.01); *A61K 9/4891* (2013.01); *A61K 31/575* (2013.01)

(58) Field of Classification Search
None
See application file for complete search history.

(56) References Cited

U.S. PATENT DOCUMENTS

| | | |
|---|---|---|
| 4,744,989 A | 5/1988 | Payne et al. |
| 5,002,936 A | 3/1991 | Lieberman et al. |
| 5,049,388 A | 9/1991 | Knight et al. |
| 5,338,761 A | 8/1994 | Nakajima et al. |
| 5,340,588 A | 8/1994 | Domb |
| 6,214,375 B1 | 4/2001 | Modi |
| 6,534,080 B2 | 3/2003 | Sands et al. |
| 6,761,901 B1 * | 7/2004 | Betageri ............. A61K 9/1277 424/450 |
| 6,849,269 B2 | 2/2005 | Betageri |
| 6,858,596 B2 | 2/2005 | Biggadike et al. |
| 6,900,235 B1 | 5/2005 | Agyin et al. |
| 7,879,360 B2 | 2/2011 | Cunningham et al. |
| 2002/0187189 A1 * | 12/2002 | Betageri ............. A61K 9/1277 424/480 |
| 2004/0115226 A1 | 6/2004 | Li et al. |
| 2004/0175417 A1 | 9/2004 | Proffitt et al. |
| 2005/0008688 A1 | 1/2005 | Betageri et al. |
| 2006/0051406 A1 | 3/2006 | Parmar |
| 2007/0053918 A1 | 3/2007 | Panzner et al. |
| 2007/0154403 A1 | 7/2007 | Skold |
| 2009/0017105 A1 | 1/2009 | Khattar et al. |
| 2009/0291129 A1 | 11/2009 | Parmar |
| 2010/0137271 A1 | 6/2010 | Chen et al. |
| 2010/0173882 A1 | 7/2010 | Giliyar et al. |
| 2011/0123625 A1 | 5/2011 | Balu-Iyer et al. |
| 2012/0027864 A1 | 2/2012 | Betageri |
| 2012/0148675 A1 | 6/2012 | Chickmath et al. |
| 2013/0045271 A1 | 2/2013 | Dadey et al. |

FOREIGN PATENT DOCUMENTS

| | | |
|---|---|---|
| EP | 648487 A | 4/1995 |
| WO | 0050007 A1 | 8/2000 |

(Continued)

OTHER PUBLICATIONS

Agnihotri et al. Drug Delivery (2010), vol. 17, pp. 92-101.*

(Continued)

*Primary Examiner* — Kendra D Carter
*Assistant Examiner* — Taina D Matos Negron
(74) *Attorney, Agent, or Firm* — J.A. Lindeman & Co., PLLC

(57) ABSTRACT

Novel testosterone formulations are disclosed where testosterone is incorporated into a phospholipid/cholesterol system to produce a proliposomal powder dispersion. The proliposomal powder dispersions of the invention may be formulated with pharmaceutically acceptable excipients to form pharmaceutical compositions. Enterically coated oral dosage forms are disclosed as are methods of treatment for testosterone replacement therapy.

17 Claims, 28 Drawing Sheets

(56) References Cited

FOREIGN PATENT DOCUMENTS

| WO | 02051426 | A2 | 7/2002 |
|---|---|---|---|
| WO | 2006/062506 | A1 | 6/2006 |
| WO | 2006060325 | A3 | 6/2006 |
| WO | 2008114274 | A1 | 9/2008 |
| WO | 2012058668 | A2 | 5/2012 |

OTHER PUBLICATIONS

Agnihotri et al.: "Controlled Release Applicatino of Multilamellar Vesicles: A Novel Drug Delivery Approache," Drug elivery, vol. 17, pp. 92-101, 2010.

Butler, et al., "Oral Testosterone Undecanoate in the Management of Delayed Puberty in Boys: Pharmacokinetics and Effects on Sexual Maturation and Growth", Journal of Clinical Endocrinology and Metabolism, 1992, vol. 75, No. 1, pp. 37-44.

PCT International Search Report and Written Opinion for International Application No. PCT/US2013/040325.

Reply to the Communication according to Art. 94(3) EPC, dated Mar. 30, 2012, in EP 05852301.0.

Ross et al.: "Pharmacokinetics and Tolerability of a Bioadhesive Buccal Testosterone Tablet and Hypogonadal Men," European Journal of Endocrinology, vol. 150, pp. 57-63, 2004.

Rowe et al.: "Handbook of Pharmaceutical Excipients," pp. 129,134, 2009.

Sessa et al. Differential Effects of Etiocholanolone on Phospholipid/Cholesterol Structures 1-10 Containing Either Testosterone or Estradiol . Biochimica Biophysica Acta (BBA)-Biomembranes. Mar. 1, 1968.[retrieved on Sep. 10, 2013). Retrieved from the Internet. <URL: http://www.sciencedirect.com/science/article/pii/0005273668901600>. Abstract.

Extended European Search Report in EP 13787438, dated Feb. 19, 2016.

* cited by examiner

PROLIPOSOMAL TESTOSTERONE FORMULATIONS

CROSS-REFERENCE TO RELATED APPLICATIONS

This application claims priority to U.S. patent application Ser. No. 15/250,169, filed Aug. 29, 2016, which is a continuation of U.S. patent application Ser. No. 14/604,985, now U.S. Pat. No. 9,445,995, filed Jan. 26, 2015, which is a continuation of U.S. patent application Ser. No. 14/149,227, now U.S. Pat. No. 8,957,053, filed Jan. 7, 2014, which is a continuation of PCT International Application Number PCT/US2013/040325, filed May 9, 2013, which claims priority to U.S. Provisional Application No. 61/644,996, filed May 9, 2012.

FIELD OF THE INVENTION

Disclosed herein are proliposomal pharmaceutical formulations for the delivery of testosterone that increase testosterone's solubility and bioavailability.

BACKGROUND

Testosterone is a BCS class II drug. Unless otherwise indicated, the term "testosterone" means testosterone that is chemically identical to the testosterone produced by the human body, i.e, "native," or "endogenous" testosterone. Testosterone may be isolated form natural sources or made by commercial synthetic processes.

SUMMARY OF THE INVENTION

Disclosed herein, in certain embodiments, are proliposomal powder dispersions comprising (a) testosterone, (b) cholesterol, and (c) at least one phospholipid. In some embodiments, (a) and (b) are present in a weight ratio (a):(b) ranging from 1:0.05 to 1:0.30 and (a), (b) and (c) are present in a weight ratio of (a):((b)+(c)) ranging from 1:1 and 1:2.5. In some embodiments, (a) and (b) are present in a weight ratio (a):(b) ranging from about 1:about 0.05 to about 1:about 0.30 and (a), (b) and (c) are present in a weight ratio of (a):((b)+(c)) ranging from about 1:about 1 and about 1:about 2.5.

Disclosed herein, in certain embodiments, are pharmaceutical compositions comprising (a) a proliposomal powder dispersion described herein, and (b) at least one pharmaceutically acceptable excipient.

Disclosed herein, in certain embodiments, are oral dosage forms comprising a pharmaceutical composition. In some embodiments, the oral dosage form is a tablet or capsule comprising (a) a proliposomal powder dispersion described herein and (b) at least one pharmaceutically acceptable excipient. In some embodiments, the tablet or capsule is coated with a delayed release coating (e.g., an enteric coating). In some embodiments, the tablet or capsule is coated with an enteric coating.

Disclosed herein, in certain embodiments, are oral testosterone dosage forms having fasting pharmacokinetic profiles that are characterized by a mean plasma concentrations of testosterone that range from about 350 to about 950 ng/dL of testosterone at about five hours after ingestion of the dosage forms. The foregoing mean plasma concentration may alternatively reported as ranging from about 4 to about 7 ng/dL/mg of testosterone at five hours after ingestion. In some embodiments, the fasting pharmacokinetic profile is characterized by a mean plasma concentration of testosterone that ranges from 350 to 950 ng/dL of testosterone at five hours after ingestion of the dosage form.

Disclosed herein, in certain embodiments, are methods of testosterone replacement therapy comprising administering a proliposomal powder dispersion disclosed herein, a pharmaceutical composition described herein, or a dosage form described herein to an individual in need thereof. Accordingly, disclosed herein are methods of treating an individual in need of testosterone therapy comprising the step of administering to the individual a therapeutically effective amount of a proliposomal powder dispersion disclosed herein, a pharmaceutical composition disclosed herein, or dosage form disclosed herein.

BRIEF DESCRIPTION OF THE FIGURES

FIG. 10 exemplifies the mean plasma testosterone concentrations over time following the oral administration of:

(a) 300 mg/kg (testosterone/rat weight) of unformulated testosterone; (b) PLF-2 comprising 300 mg/kg of testosterone; (c) PLF-2 comprising 150 mg/kg of testosterone; and (d) PLF-4 comprising 300 mg/kg of testosterone to male fasted rats. See Example 5.

Figure 11:
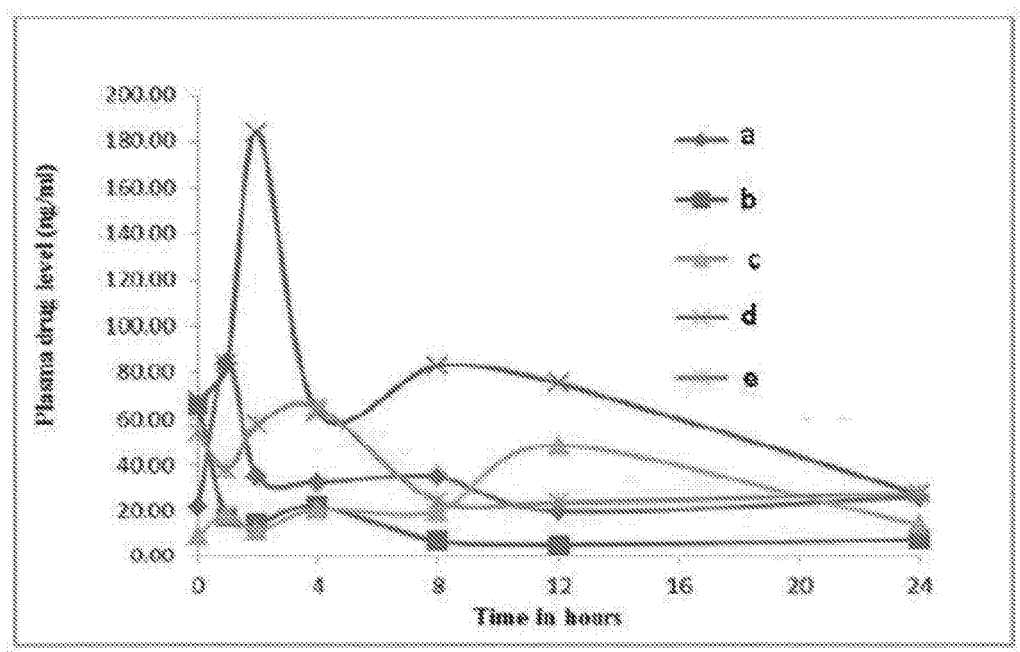

FIG. 11 exemplifies the mean plasma testosterone concentrations over time following the oral administration of: a) 300 mg/kg (testosterone/rat weight) of unformulated testosterone; (b) 31 mg/kg (testosterone/rat weight) of unformulated testosterone; (c) PLF-2 comprising 31 mg/kg of testosterone; (d) PLF-2 comprising 15.5 mg/kg of testosterone; and (e) PLF-2 comprising 7.75 mg/kg of testosterone male fasted rats. See Example 5.

Figure 12:
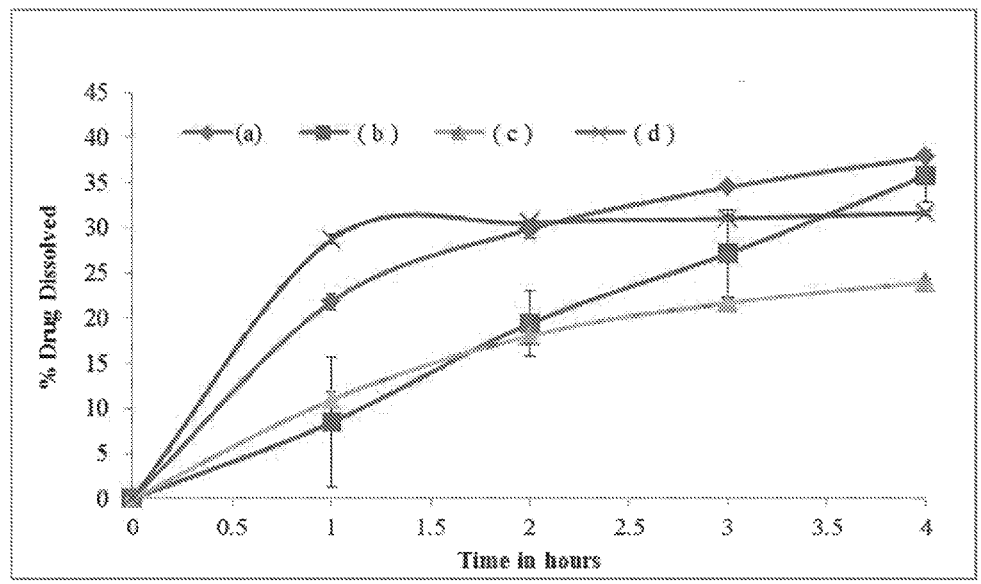

FIG. 12 exemplifies the in vitro testosterone dissolution profiles of the following formulations: (a) encapsulated PLF-5 with Avicel® PH 101 and 1% Explotab® disintegrant; (b) tableted PLF-5 with Avicel® PH 101, SD lactose, Mg stearate; and 1% Explotab® disintegrant; (c) tableted PLF-5 with Avicel® PH 101, Mg stearate; and 5% Explotab® disintegrant; and (d) powdered PLF-5 with Avicel® PH 101, Mg stearate; and 5% Explotab® disintegrant. See Example 6.

Figure 13:
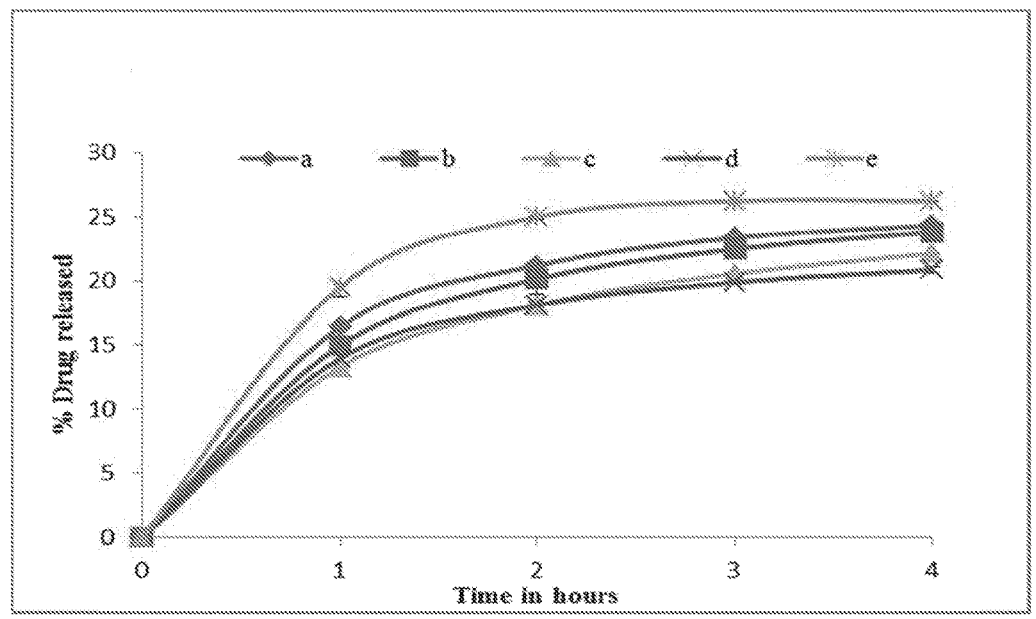

FIG. 13 exemplifies the in vitro testosterone dissolution profiles of the following tableted formulations: (a) PLF-6 with Avicel® PH 101, Mg stearate; and Explotab® disintegrant; (b) PLF-6 with 20% Pearlitol®, Avicel® PH 102, Mg stearate; and Explotab® disintegrant; (c) PLF-6 with 10% Pearlitol®, Avicel® PH 102, Mg stearate; and Explotab® disintegrant; (d) PLF-7 with Avicel® PH 102, Mg stearate; and Explotab® disintegrant; and (e) PLF-6 with Avicel® PH 101, Mg stearate; and Explotab® disintegrant. Dissolution in (e) was performed in a Type II apparatus at 75 rpm, rather then 50 rpm, as was done for (a)-(d). See Example 7.

Figure 14:
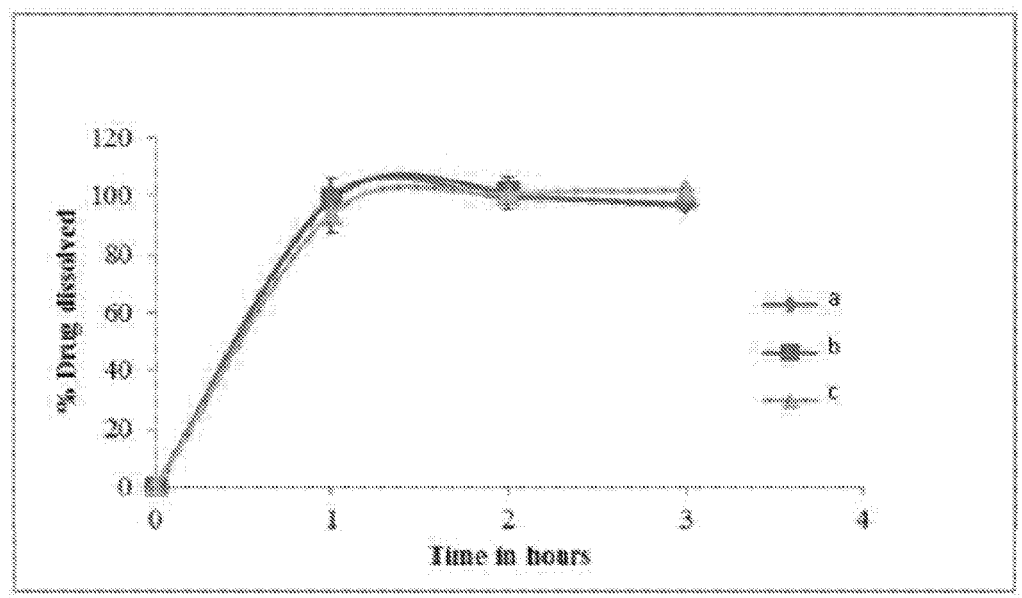

FIG. 14 exemplifies the in vitro testosterone dissolution profiles of the following formulations: (a) encapsulated PLF-2 with Avicel® PH 101; (b) tableted PLF-6 with Avicel® PH 101, Mg stearate; and Explotab® disintegrant; and (c) PLF-8 (unformulated testosterone control). See Example 8 and Table 9.

Figure 15:
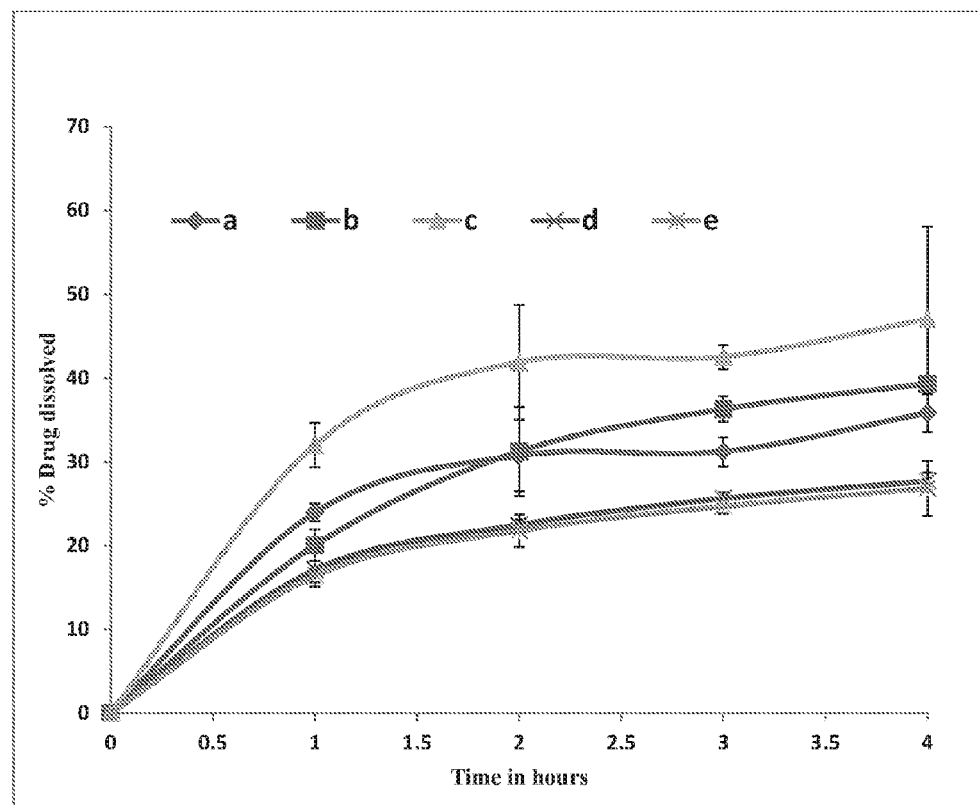

FIG. 15 exemplifies the in vitro testosterone dissolution profiles of the following encapsulated formulations: (a) PLF-9 with Avicel® PH 102 (1:2); (b) PLF-9 with Avicel® PH 102 (1:0.5); (c) PLF-9 with Avicel® PH 102 (1:1); (d) PLF-9 with Avicel® PH 102 (1:0.6); and (e) PLF-9 with Avicel® PH 102 (1:0.6) and Explotab® disintegrant. See Example 9 and Table 10.

Figure 16:
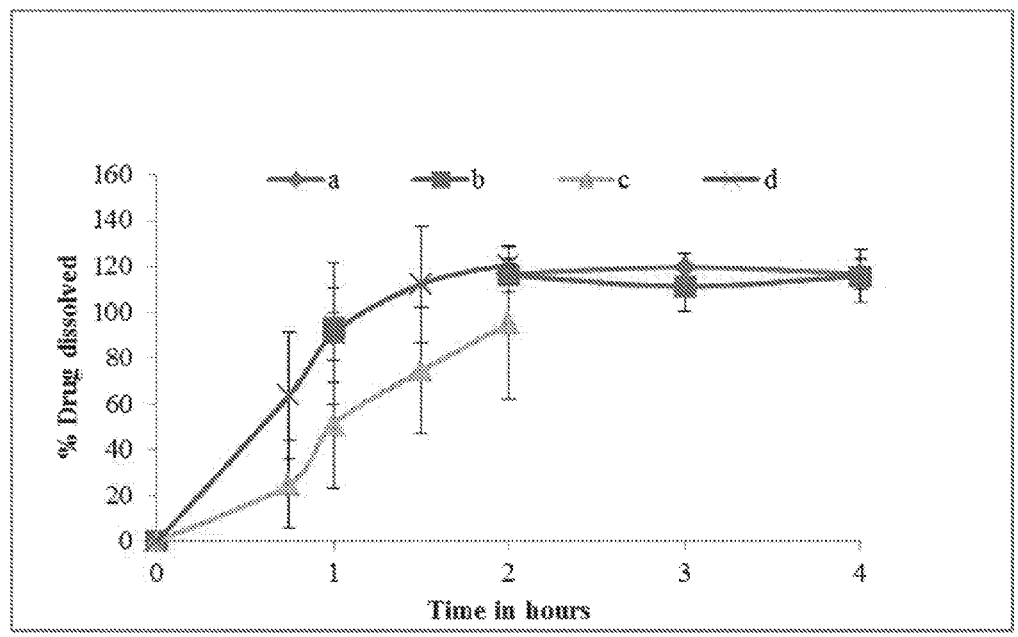

FIG. 16 exemplifies the in vitro testosterone dissolution profiles of the following encapsulated formulations and percentages of SLS in the dissolution media: (a) PLF-11 with Avicel® PH 102 dissolved in 1% SLS; (b) PLF-11 with Avicel® PH 102 dissolved in 2% SLS; (c) PLF-12 with Avicel® PH 102 and Explotab® disintegrant dissolved in 0.5% SLS; and (d) PLF-12 with Avicel® PH 102 and Explotab® disintegrant dissolved in 1% SLS. See Example 10 and Table 11.

Figure 17:
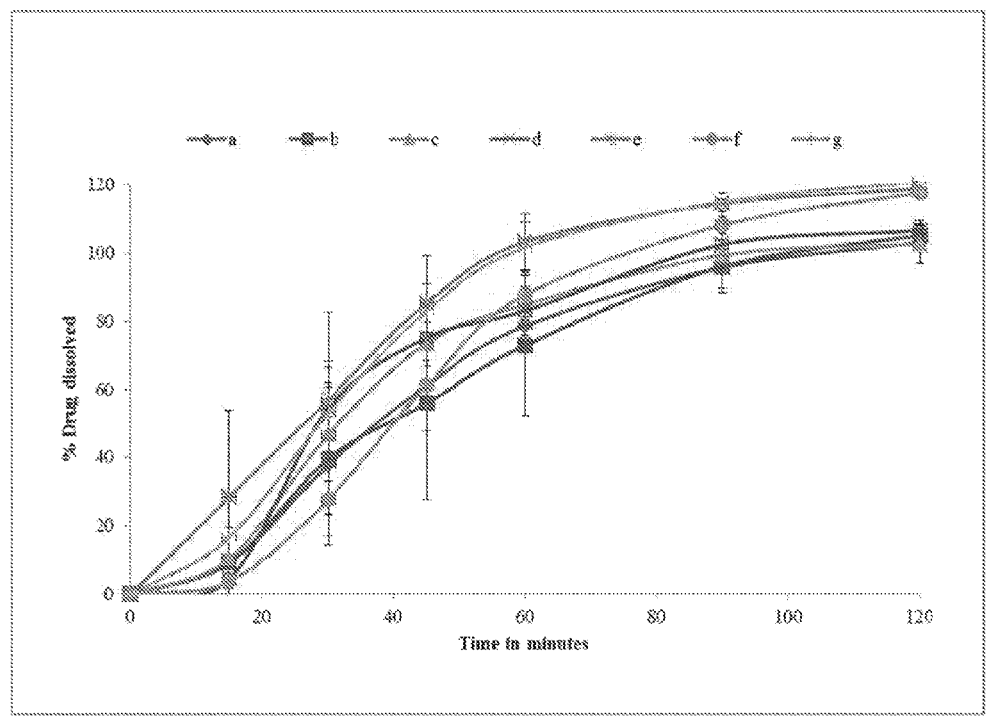

FIG. 17 exemplifies the in vitro testosterone dissolution profiles of the following encapsulated formulations: (a) PLF-16 with Avicel® PH 102 and Explotab® disintegrant; (b) PLF-17 with Avicel® PH 102 and Explotab® disintegrant; (c) PLF-18 with SMCC and Explotab® disintegrant; (d) PLF-19 with DCP and Explotab® disintegrant; (e) PLF-20 with Avicel® PH 102 and Explotab® disintegrant; (f) PLF-21 with SMCC and Explotab® disintegrant; and (g) PLF-22 with DCP and Explotab® disintegrant. See Example 12, and Table 13.

Figure 18:
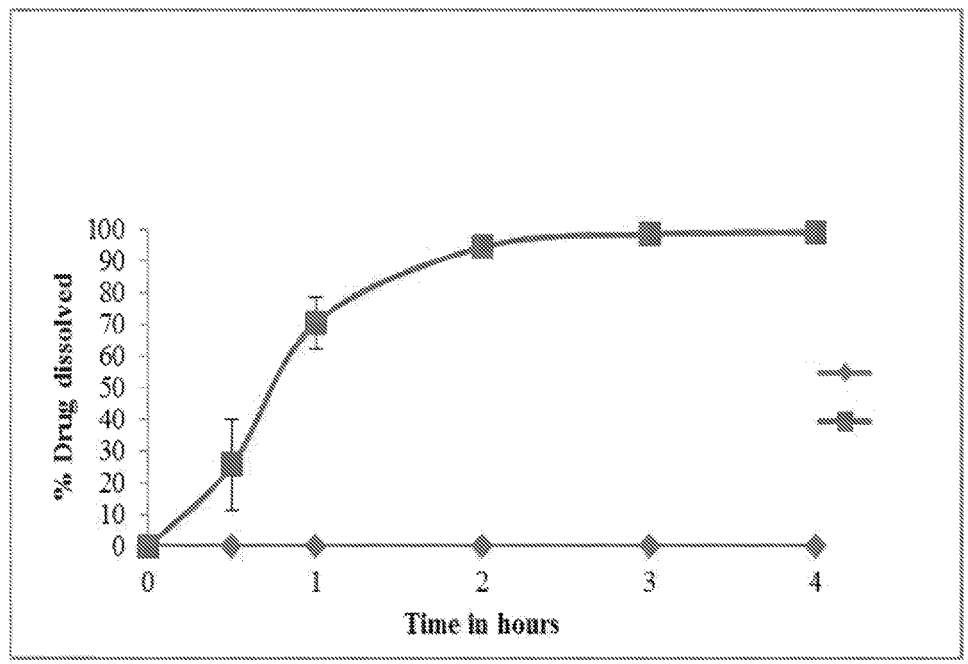

FIG. 18 exemplifies the in vitro testosterone dissolution profiles of encapsulated (a) PLF 24 (placebo) enteric coated and (b) enterically coated PLF 25 containing testosterone. See Example 13 and Table 14.

Figure 19:
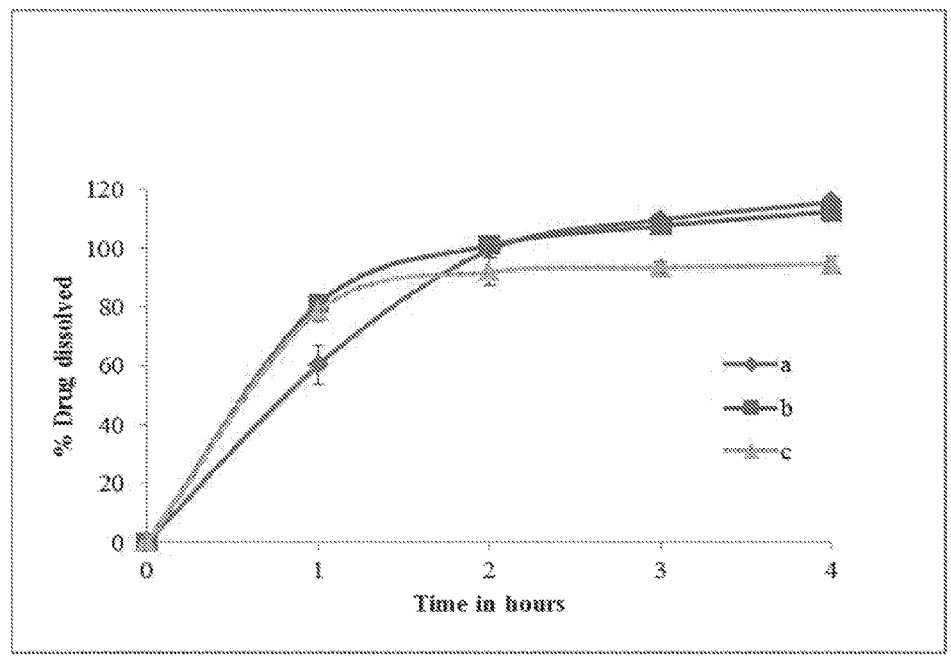

FIG. 19 exemplifies the in vitro testosterone dissolution profiles of the following encapsulated formulations: (a) enterically-coated PLF-26; (b) enterically-coated PLF-27; and (c) uncoated PLF-29. See Example 14 and Table 18.

Figure 20:
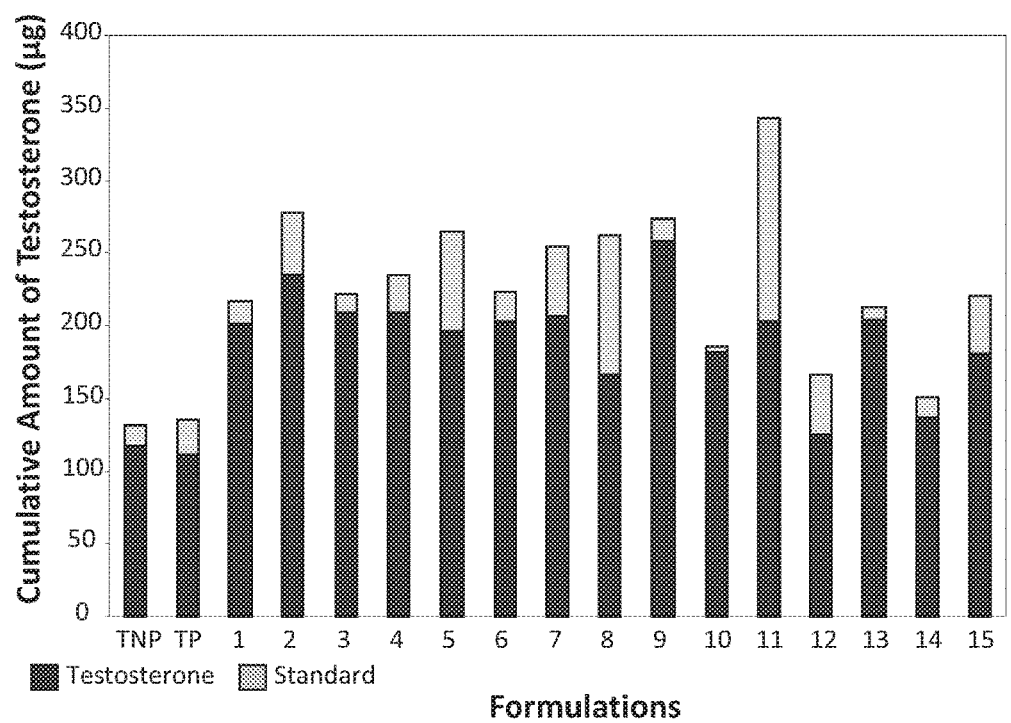

FIG. 20 exemplifies the transport of testosterone released from the formulations listed in Table 20 across a monolayer of Caco-2 Cells. See Example 15B and Table 20.

Figure 21:
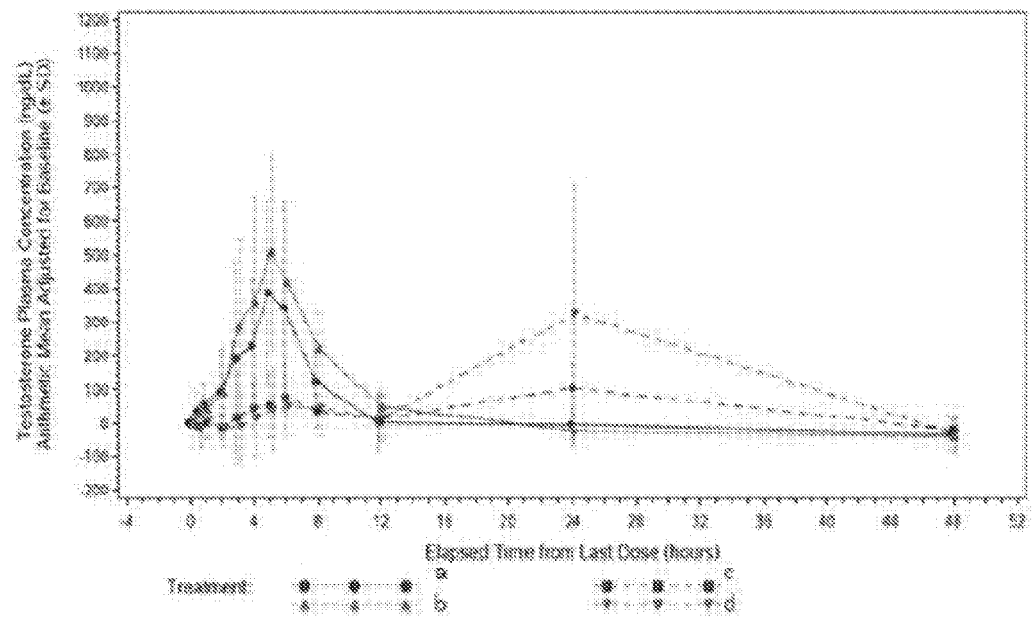

FIG. 21 exemplifies the mean plasma concentrations of testosterone over time obtained from human patients with hypogonadism following the oral administration of either 120 mg or 240 mg of testosterone in humans as described in the pharmacokinetics study of Example 16. Testosterone (T) concentrations are adjusted for baseline. Plasma testosterone concentrations were determined at the times shown after administration of: (a) 120 mg of T under fasting conditions; (b) 240 mg of T under fasting conditions; (c) 120 mg of T under fed conditions; and (d) 240 mg of T under fed conditions.

Figure 22:
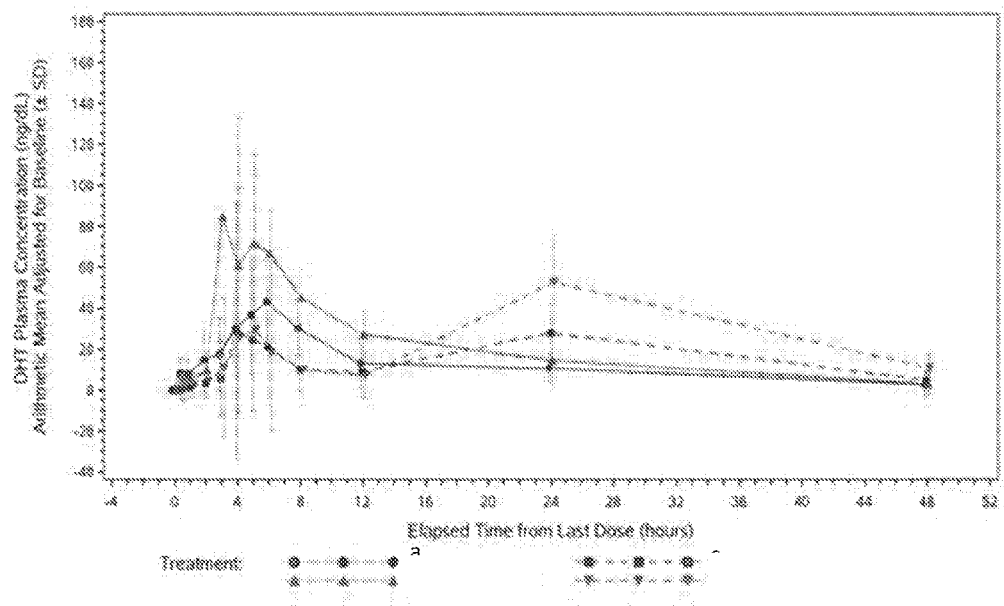

FIG. 22 exemplifies the mean plasma concentrations of the testosterone metabolite DHT over time obtained from human patients with hypogonadism following the oral administration of either 120 mg or 240 mg of testosterone that has been formulated as provided in Table 20. DHT concentrations are adjusted for baseline. Plasma DHT concentrations were determined at the times shown after administration of either: (a) 120 mg of formulated T under fasting conditions; (b) 240 mg of formulated T under fasting conditions; (c) 120 mg of formulated T under fed conditions; and (d) 240 mg of formulated T under fed conditions.

Figure 23:
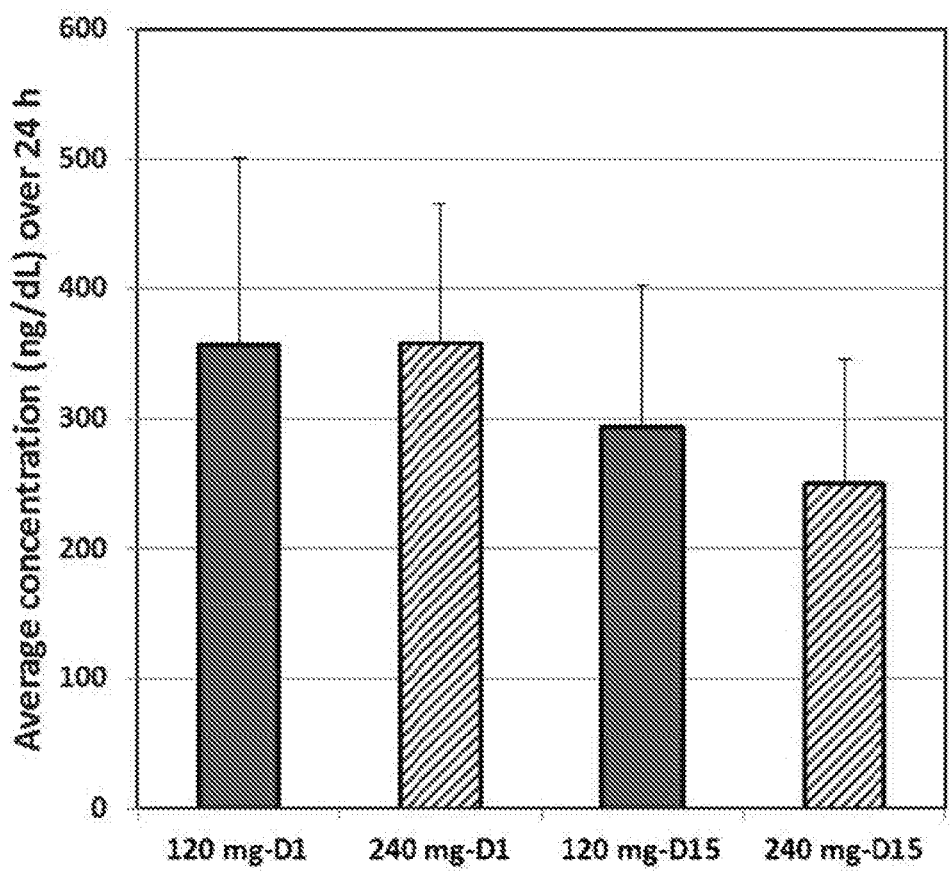

FIG. 23 exemplifies mean plasma testosterone concentrations (24 h profile) in human subjects with hypogonadism after receiving twice-daily, oral administrations of either 120 mg or 240 mg of formulated testosterone (T) for a period of time of one day (D1) and fifteen days (D15). The 120 mg dosage form used to obtain the data is described in Example 18. The 240 mg doses were given by administering two 120 mg doses.

Figure 24:
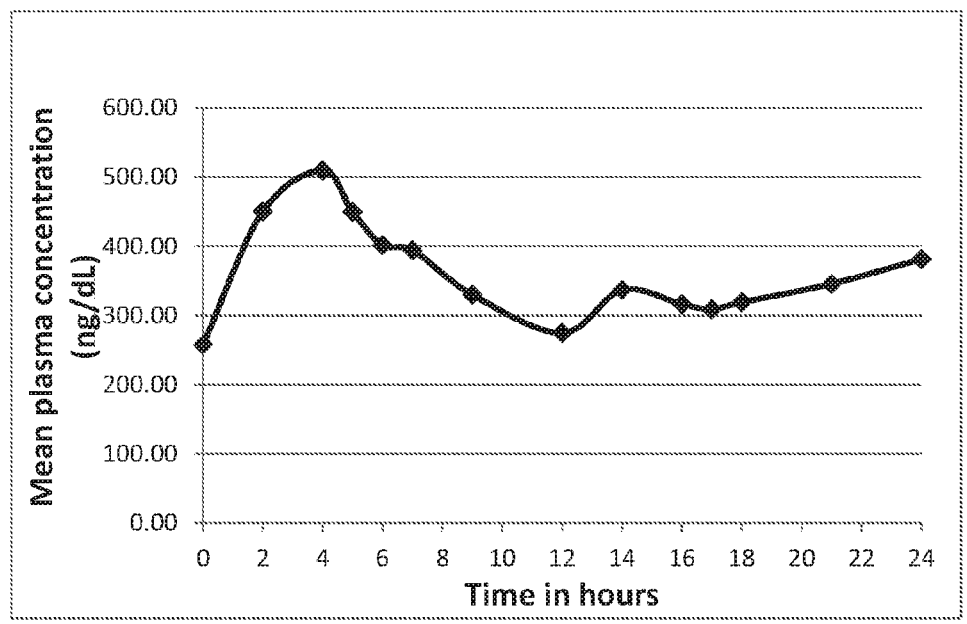

FIG. 24 exemplifies mean plasma testosterone (T) concentrations of human subjects with hypogonadism every two hours over the first 24 hours of a 15 day long treatment regimen of being administered a 120 mg testosterone dosage form like the dosage form that is described in Example 18, herein, twice-daily.

Figure 25:
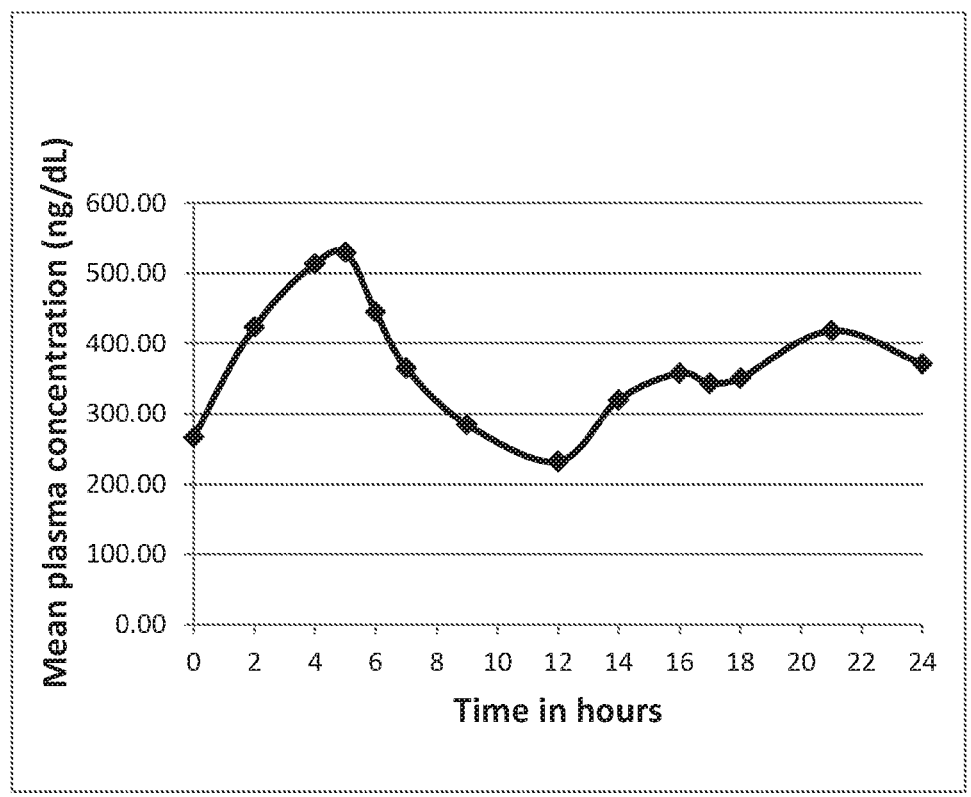

FIG. 25 exemplifies mean plasma testosterone (T) concentrations of human subjects with hypogonadism every two hours over the first 24 hours of a 15 day long treatment regimen of being administered the 240 mg testosterone proliposomal dosage form that is described in Example 18, herein, twice-daily.

Figure 26:
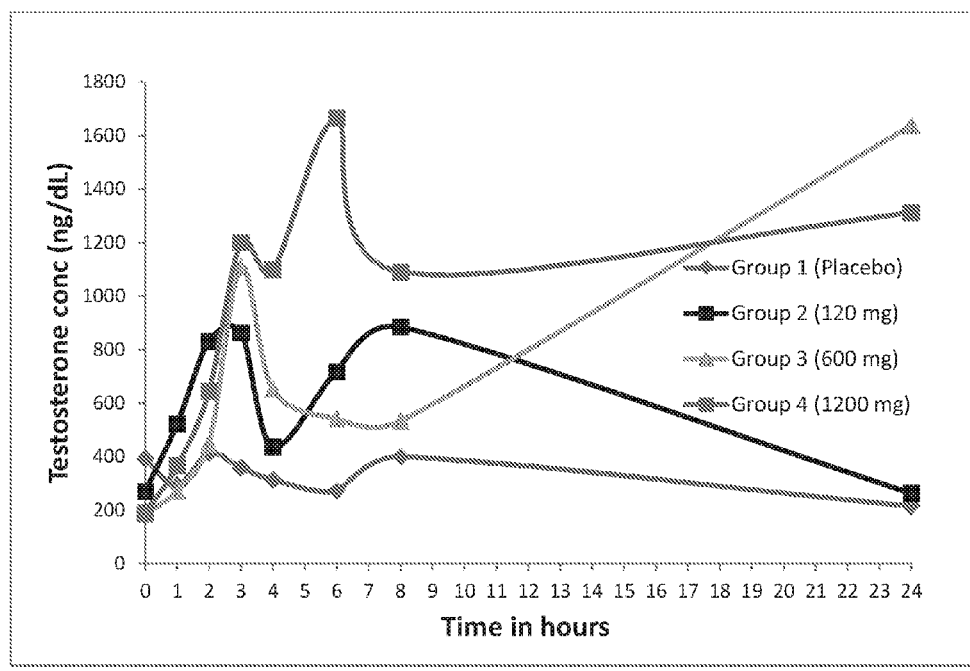

FIG. 26 exemplifies the mean plasma testosterone concentrations in beagle dogs over the 24 hour period of the first day of after orally administering: (a) placebo, (b) 120 mg, (c) 600 mg, or (d) 1200 mg of testosterone that had been formulated according to the composition and method of preparation of the proliposomal testosterone dosage form described in Example 18.

Figure 27:
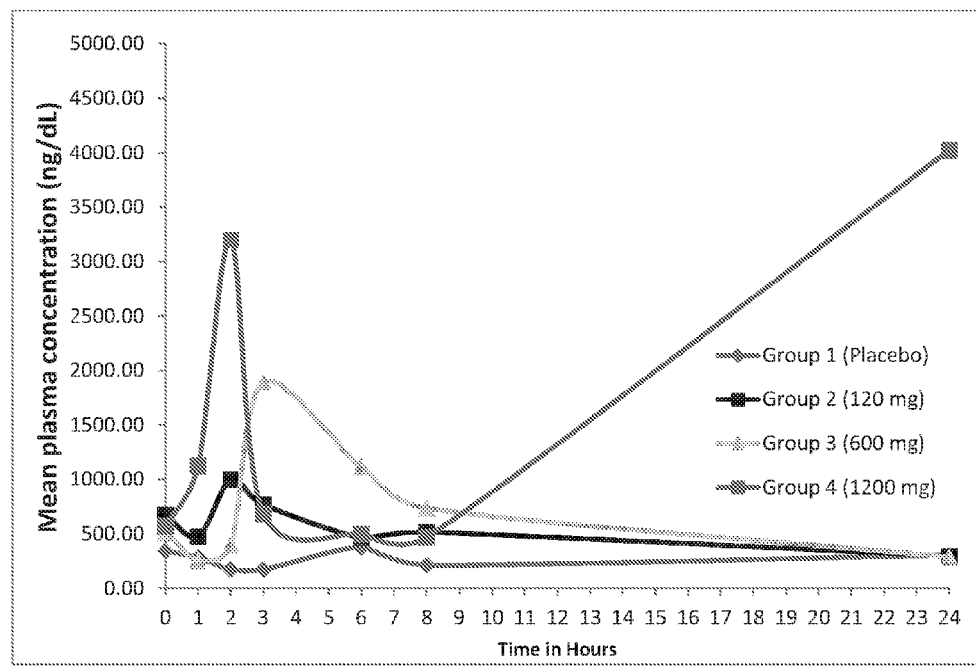

FIG. 27 exemplifies the mean plasma testosterone concentrations in beagle dogs over a 24 hour period of the $57^{th}$ day after orally administering (a) placebo, (b) 120 mg, (c) 600 mg, or (d) 1200 mg of testosterone that had been formulated according to the composition and method of preparation of the proliposomal testosterone dosage form described in Example 18.

Figure 28:
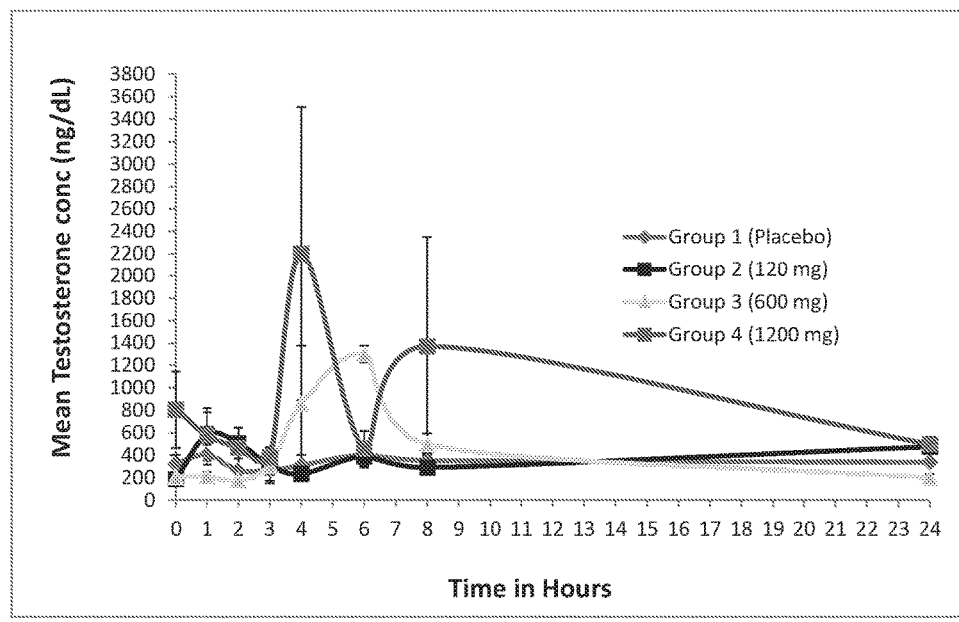

FIG. 28 exemplifies the mean plasma testosterone concentrations in beagle dogs over a 24 hour period of the $91^{st}$ day after orally administering (a) placebo, (b) 120 mg, (c) 600 mg, or (d) 1200 mg of testosterone that had been formulated according to the composition and method of preparation of the proliposomal testosterone dosage form described in Example 18.

DETAILED DESCRIPTION

Testosterone and Testosterone Deficiency

Disclosed herein, in certain embodiments, are compositions and methods of treating testosterone deficiency. Further disclosed herein, in certain embodiments, are methods and compositions for treating diseases, disorders, or conditions characterized by testosterone deficiency. A number of situations (including aging, the use of androgen depletion therapy for the treatment of prostate cancer, or genetic abnormalities) may result in abnormally low levels of testosterone (i.e., testosterone deficiency). The consequences associated with testosterone deficiency in men include, but are not limited to, increased fat mass, decreased muscle mass and strength, sexual dysfunction, and osteoporosis. Testosterone deficiency may also be associated with the development of a variety of metabolic and cardiovascular conditions.

As a man ages, the amount of testosterone in his body gradually declines. This natural decline starts after age 30 and continues throughout life. Other causes of low testosterone levels include, but are not limited to: injury, infection, or loss of the testicles; chemotherapy or radiation treatment for cancer; genetic abnormalities such as Klinefelter's Syndrome (extra X chromosome); hemochromatosis (too much iron in the body); dysfunction of the pituitary gland (a gland in the brain that produces many important hormones); inflammatory diseases such as sarcoidosis (a condition that causes inflammation of the lungs); medications, especially hormones used to treat prostate cancer and corticosteroid drugs; chronic illness; chronic kidney failure; liver cirrhosis; stress; alcoholism; obesity (especially abdominal); and congenital conditions, such as Kallman's Syndrome.

Male hypogonadism, or testosterone deficiency syndrome (TDS), results from a failure of the testes to produce adequate androgen. Patients have low circulating testosterone in combination with clinical symptoms such as fatigue, erectile dysfunction, and body composition changes. The cause may be primary (genetic anomaly, Klinefelter's syndrome) or secondary (defect in hypothalamus or pituitary), but often presents with the same symptomotology. In the older patient, androgen deficiency of the aging male (ADAM) is an important cause of secondary hypogonadism because testosterone levels decline progressively after age 40. Hypogonadal patients have alterations not only in sexual function and body composition, but also in cognition and metabolism. Regardless of etiology, hypogonadal patients who are both symptomatic and who have clinically significant alterations in laboratory values are candidates for treatment. The goal of hormone replacement therapy in these men is to restore hormone levels to the normal range and to alleviate symptoms suggestive of hormone deficiency. This can be accomplished in a variety of ways, although most commonly testosterone replacement therapy (TRT) is employed. Disclosed herein, in certain embodiments, are proliposomal powder dispersions for treating hypogonadism comprising: (a) testosterone, (b) cholesterol, and (c) at least one phospholipid, wherein (a) and (b) are present in a weight ratio (a):(b) ranging from 1:0.05 to 1:0.30 and (a), (b) and (c) are present in a weight ratio of (a):((b)+(c)) ranging from 1:1.0 and 1:2.5. Further, disclosed herein, in certain embodiments, are methods of treating hypogonadism in an individual in need thereof comprising administering to the individual a proliposomal powder dispersion comprising: (a) testosterone, (b) cholesterol, and (c) at least one phospholipid, wherein (a) and (b) are present in a weight ratio (a):(b) ranging from 1:0.05 to 1:0.30 and (a), (b) and (c) are present in a weight ratio of (a):((b)+(c)) ranging from 1:1.0 and 1:2.5.

Klinefelter's syndrome, (47XXY, or XXY syndrome) is a condition in which human males have an extra X chromosome. In humans, 47XXY is the most common sex chromosome aneuploidy in males and the second most common condition caused by the presence of extra chromosomes. The physical traits of the syndrome become more apparent after the onset of puberty, if at all. Principal effects include hypogonadism and reduced fertility. A variety of other physical and behavioural differences and problems are common, though severity varies and many XXY boys have few detectable symptoms. Not all XXY boys and men develop the symptoms of Klinefelter syndrome. The genetic variation is irreversible. Testosterone treatment is an option for some individuals who desire a more masculine appearance and identity. Disclosed herein, in certain embodiments, are proliposomal powder dispersions for treating Klinefelter's syndrome comprising: (a) testosterone, (b) cholesterol, and (c) at least one phospholipid, wherein (a) and (b) are present in a weight ratio (a):(b) ranging from 1:0.05 to 1:0.30 and (a), (b) and (c) are present in a weight ratio of (a):((b)+(c)) ranging from 1:1 and 1:2.5. Further, disclosed herein, in certain embodiments, are methods of treating Klinefelter's syndrome in an individual in need thereof comprising administering to the individual a proliposomal powder dispersion comprising: (a) testosterone, (b) cholesterol, and (c) at least one phospholipid, wherein (a) and (b) are present in a weight ratio (a):(b) ranging from 1:0.05 to 1:0.30 and (a), (b) and (c) are present in a weight ratio of (a):((b)+(c)) ranging from 1:1.0 and 1:2.5.

Other diseases or conditions where the level of endogenous testosterone is insufficient include, but are not limited to, erectile dysfunction, idiopathic gonadotropin deficiency, pituitary hypothalamus injury due to tumours, osteoporosis, diabetes mellitus, chronic heart failure, chemotherapy, hemochromatosis, cirrhosis, renal failure, AIDS, sarcoidosis, Kallman's Syndrome, androgen receptor defects, 5-alpha reductase deficiency, myotonic dystrophy, cryptorchidism, mumps orchitis, aging, fertile eunuch syndrome, and pituitary disorders. Disclosed herein, in certain embodiments, are proliposomal powder dispersions for treating diseases, disorders or conditions where the level of endogenous testosterone is insufficient comprising: (a) testosterone, (b) cholesterol, and (c) at least one phospholipid, wherein (a) and (b) are present in a weight ratio (a):(b) ranging from 1:0.05 to 1:0.30 and (a), (b) and (c) are present in a weight ratio of (a):((b)+(c)) ranging from 1:1 and 1:2.5. Further, disclosed herein, in certain embodiments, are methods of treating diseases, disorders or conditions where the level of endogenous testosterone is insufficient comprising administering to an individual in need thereof a proliposomal powder dispersion comprising: (a) testosterone, (b) cholesterol, and (c) at least one phospholipid, wherein (a) and (b) are present in a weight ratio (a):(b) ranging from 1:0.05 to 1:0.30 and (a), (b) and (c) are present in a weight ratio of (a):((b)+(c)) ranging from 1:1 and 1:2.5. In embodiments of any of the aforementioned, the disease, disorder or condition where the level of endogenous testosterone is insufficient is erectile dysfunction, idiopathic gonadotropin deficiency, pituitary hypothalamus injury due to tumours, osteoporosis, diabetes mellitus, chronic heart failure, chemotherapy, hemochromatosis, cirrhosis, renal failure, AIDS, sarcoidosis, Kallman's Syndrome, androgen receptor defects, 5-alpha reductase deficiency, myotonic dystrophy, cryptorchidism, mumps orchitis, aging, fertile eunuch syndrome, and pituitary disorders. In embodiments of any of the aforementioned, the disease, disorder or condition where the level of endogenous testosterone is insufficient is erectile dysfunction. In embodiments of any of the aforementioned, the disease, disorder or condition where the level of endogenous testosterone is insufficient is diabetes mellitus. In embodiments of any of the aforementioned, the disease, disorder or condition where the level of endogenous testosterone is insufficient is chronic heart failure.

The therapeutic effectiveness of a drug depends on its bioavailability, i.e., the measure of the rate and extent to which the drug or active moiety is absorbed from a drug product and becomes available at the site of action. Poor bioavailability of a drug depends on many factors, particularly important factors include drug solubility in the gastrointestinal fluid (GI fluid), drug stability in the GI region (acid and enzyme stability), and systemic concentration of the drug without significant loss to the hepatic portal system before reaching the rest of the body (the first pass effect). If a drug fails in one of these aspects, the drug may not be sufficiently available for biological activity.

The FDA's Biopharmaceutics Classification System (BCS) provides guidance for predicting oral drug absorption by taking into account a drug's aqueous solubility and its tissue permeability. Specifically, the BCS divides drugs into classes I through IV based on their aqueous solubility and permeability. Class I drugs are highly soluble and highly permeable, class II drugs have low solubility, but are highly permeable, class III drugs are highly soluble but poorly permeable; and class IV drugs are low soluble and poorly permeable.

Testosterone is a BCS class II drug. Unless otherwise indicated, the term "testosterone" means testosterone that is chemically identical to testosterone produced by the human body, i.e, "native," or "endogenous" testosterone, or a testosterone derivative. Testosterone may be isolated form natural sources or made by commercial synthetic processes. In some embodiments, the testosterone used in the proliposomal powder dispersions described herein is testosterone that is chemically identical to testosterone produced by the human body, i.e, "native," or "endogenous" testosterone, or a testosterone derivative. In some embodiments, the testosterone used in the proliposomal powder dispersions described herein is a testosterone derivative, wherein the amount of a testosterone derivative in the proliposomal dispersion corresponds to a molar amount of testosterone allowed in a proliposomal dispersion based on the range of weight:weight ratios of testosterone to the other proliposomal dispersion components that are specified herein. In some embodiments, the testosterone used in the proliposomal powder dispersions described herein is a testosterone derivative selected from: testosterone undecanoate (or testosterone undecylate), epitestosterone, fluoxymesterone, mesterolone, methyltestosterone, 19-nortestosterone, 17-alpha methyl testosterone, 7-alpha alkyl 19-nortestosterone, or testosterone enanthate. In some embodiment, the testosterone used in the pharmaceutical compositions described herein is esterified at the 17-beta hydroxyl. In some embodiments, esterification of 17-beta hydroxyl group increases hydrophobicity. In some embodiment, the testosterone used in the proliposomal powder dispersions described herein is a salt of testosterone. Examples of testosterone salts include, but are not limited to: testosterone acetate and testosterone propionate. In some embodiments, a proliposomal powder dispersion described herein comprises testosterone that is chemically identical to testosterone produced by the human body, i.e, "native," or "endogenous" testosterone, a testosterone derivative or testosterone salt, or individual combinations thereof.

A major obstacle to successful commercialization of testosterone is the difficulty of enhancing not only its dissolution rate but also the extent of its dissolution. Indeed, the fact that BCS class II drugs, like testosterone, are poorly soluble is often associated with low and highly variable bioavailabilities of these drugs. Another drawback of administering testosterone is that much of ingested testosterone is metabolized before it reaches its target(s). More specifically, the hepatic portal system that carries testosterone from the intestine to the liver where it is metabolized before reaching systemic circulation. The so-called name given to this phenomenon is "the first pass effect." In addition to the fact that the metabolized drug does not provide the same effect as that of the parent drug, the first pass effect may also cause hepato-toxicity. As discussed below, different approaches have been developed in order to avoid the first pass effect that is associated with administering testosterone.

One approach to avoiding the first pass effect during testosterone treatment has been to use prodrug forms of testosterone and other testosterone derivatives that are not subject to the first pass effect. Indeed, ester prodrugs of testosterone, such as, testosterone propionate, testosterone cypionate, testosterone enanthate, testosterone decanoate, and testosterone undecanoate have been used as substitutes for testosterone, e.g., sold under the Restandol® and Andriol® tradenames. In the United States, another testosterone derivative is currently available in different dosage forms: testosterone enanthate for intramuscular injection (under the Delatestryl® tradename), topical solution (under the Axiron® tradename), buccal patch (under the Striant® tradename), topical gel (under the AndroGel® and AndroGel® 1.62% tradenames).

Another approach to testosterone treatment is based on the well-established observation that circulating testosterone in a healthy male is metabolized to dihydrotestosterone (DHT) and to estradiol. Typically, the ratio of testosterone to DHT is 10:1 and to that to estradiol is 200:1. Changes in these ratios affect androgenic activity. As such, testosterone derivatives that restore the ratio of testosterone to its metabolites have been used clinically. These types of testosterone derivatives, such as alkylated derivatives used for oral therapy (methyltestosterone), are metabolized slowly, thus allowing higher levels of DHT, which, in turn, change the circulating testosterone:DHT ratios. However, prolonged use of alkylated testosterone derivatives has been associated with development of severe hepatotoxicity.

Yet another approach to testosterone treatment is the utilization of liposomes as effective oral carrier systems for testosterone. Liposomes absorbed by the intestinal lymphatic system are incorporated into chylomicrons (i.e., a type of lipoprotein particle formed in the absorptive cells of the small intestine). The chylomicrons, together with remaining liposomes, bypass the liver (portal circulation), and travel through the lymph system to the subclavian vein. In the blood stream, these liposomes are digested by lipoprotein lipases derived from the capillary walls, which releases the drug. However, in spite of the advantages liposome drug delivery offer, they also face obstacles presented by the gastrointestinal digestive fluids, pH variation, bile salts and lipolytic and proteolytic enzymes. For example, typical liposomes are mostly broken down by the gastric acids, rendering the delivery system ineffective for oral administration.

One approach to liposome-mediated drug delivery that offers the advantages of liposomes, but minimizes the destructive effect of the gastrointestinal system on liposomes, is to use a proliposomal drug delivery system. By employing this approach, a poorly-water soluble drug such as testosterone can be incorporated into a dry, free-flowing powder that will form liposome-encapsulated testosterone in an aqueous environment. Because proliposomal formulation are dry powders, they, unlike liposomes, can be coated with a delayed release coating (e.g., an enteric coating)" that will protect the formulation until it reaches the less hostile environment of the small intestine, where liposomes can form in a dramatically less destructive environment. A need exists to develop proliposomal pharmaceutical formulations that increase the solubilities of testosterone and have it available at the site of action.

In some embodiments, the proliposomal powder dispersions and the pharmaceutical compositions disclosed herein are administered to an individual in need of testosterone replacement therapy. In some embodiments, the proliposomal powder dispersions and the pharmaceutical compositions disclosed herein are administered to an individual in need thereof to treat erectile dysfunction, hypogonadism, idiopathic gonadotropin deficiency, pituitary hypothalamus injury due to tumours, osteoporosis, diabetes mellitus, chronic heart failure, chemotherapy, Klinefelter's Syndrome, hemochromatosis, cirrhosis, renal failure, AIDS, sarcoidosis, Kallman's Syndrome, androgen receptor defects, 5-alpha reductase deficiency, myotonic dystrophy, cryptorchidism, mumps orchitis, aging, fertile eunuch syndrome, pituitary disorders, and other conditions where the level of endogenous testosterone is insufficient. Accordingly, disclosed herein, in certain embodiments, are methods of treating an individual in need of testosterone therapy comprising administering to the individual a therapeutically effective amount of the proliposomal powder dispersion described herein. In some embodiments, the proliposomal powder dispersion or pharmaceutical composition is administered orally and in a dosage form described herein.

Pharmaceutical Compositions

The pharmaceutical compositions described herein are formulated for delivery by any suitable method. Exemplary forms of the pharmaceutical compositions described herein, include, a tablet, a pill, a powder, a capsule (including both soft or hard capsules made from animal-derived gelatin or plant-derived HPMC), a sachet, a troche, pellets, granules, emulsions, and solutions. These pharmaceutical compositions described herein can be manufactured by conventional techniques known in the pharmaceutical arts.

Conventional techniques for preparing pharmaceutical compositions described herein include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., prilling, spray drying, pan coating, melt granulation, granulation, wurster coating, tangential coating, top spraying, tableting, extruding, coacervation and the like.

Disclosed herein, in certain embodiments, are novel testosterone formulations where a pharmaceutically effective amount of testosterone is incorporated into a phospholipid/cholesterol system to produce a proliposomal powder dispersion. In some embodiments, the proliposomal powder dispersions are contained in delayed-release capsule for oral administration and to withstand the acidic environment in the stomach. In some embodiments, the proliposomal powder dispersions are contained in an enterically-coated capsule for oral administration and to withstand the acidic environment in the stomach. Upon contact with small intestinal fluid, the proliposomal powder dispersion is dispersed and hydrated, leading to the formation of liposomes and uptake of the testosterone through the lymphatic system. In some embodiments, the compositions disclosed herein reduce the first-pass side effect that is commonly associated with oral administration of testosterone.

In some embodiments, a proliposomal powder dispersion disclosed herein comprises (a) testosterone, (b) cholesterol, and (c) at least one phospholipid. As used herein, a "proliposomal powder dipsersion" means a mixture of at least (a) testosterone, (b) cholesterol, and (c) at least one phospholipid, dispersed one in another, and which forms a liposome upon contact with an aqueous environment. As shown in examples below, proliposomal powder dispersions with low amounts of cholesterol possess improved permeability with less standard deviation as compared to powder dispersions with no cholesterol or powder dispersions containing relatively large amounts of cholesterol.

In some embodiments, testosterone (a) and cholesterol (b) are present in a weight ratio of (a):(b) that ranges from about 1:about 0.05 to about 1:about 0.3. In some embodiments, testosterone (a) and cholesterol (b) are present in a weight ratio of (a):(b) that ranges from 1:0.05 to 1:0.3. In some embodiments, testosterone (a) and cholesterol (b) are present in a weight ratio of (a):(b) is about 1:about 0.05, about 1:about 0.1, about 1:about 0.15, about 1:about 0.2, about 1:about 0.25, or about 1:about 0.3. In some embodiments, testosterone (a) and cholesterol (b) are present in a weight ratio of (a):(b) is 1:0.05, 1:0.1, 1:0.15, 1:0.2, 1:0.25, or 1:0.3. In some embodiments, the ratio of testosterone to (b) and the at least one phospholipid (c), i.e., (a):((b)+(c)) range from about 1:about 1 to about 1:about 2.5. In some embodiments, the ratio of testosterone to (b) and the at least one phospholipid (c), i.e., (a):((b) (c)) range from 1:1 to 1:2.5. In some embodiments, the ratio of testosterone to (b) and the at least one phospholipid (c), i.e., (a):((b)+(c)) is about 1:about 1, about 1:about 1.1, about 1:about 1.2, about 1:about 1.3, about 1:about 1.4, about 1:about 1.5, about 1:about 1.6, about 1:about 1.7, about 1:about 1.8, about 1:about 1.9, about 1:about 2.0, about 1:about 2.1, about 1:about 2.2, about 1:about 2.3, about 1:about 2.4, or about 1:about 2.5. In some embodiments, the ratio of testosterone to (b) and the at least one phospholipid (c), i.e., (a):((b)+(c)) is 1:1, 1:1.1, 1:1.2, 1:1.3, 1:1.4, 1:1.5, 1:1.6, 1:1.7, 1:1.8, 1:1.9, 1:2.0, 1:2.1, 1:2.2, 1:2.3, 1:2.4, or 1:2.5. The weight ratios of the components in the powder dispersion may be varied within these ranges. In some embodiments, the weight ratios of testosterone:cholesterol:at least one phospholipid are: about 1:about 0.1:about 0.9; about 1:about 0.2:about 1.8; and about 1:about 0.2:about 1.3. In some embodiments, the weight ratios of testosterone:cholesterol: at least one phospholipid are: 1:0.1:0.9; 1:0.2:1.8; and 1:0.2:1.3. In certain embodiments, the weight ratio of (a):(b) ranges from about 1:about 0.1 to about 1:about 0.2 and (a), (b) and the at least one phospholipid (c) are present in a weight ratio of (a):((b)+(c)) ranging from about 1:about 1.1 and about 1:about 2. In certain embodiments, the weight ratio of (a):(b) ranges from 1:0.1 to 1:0.2 and (a), (b) and the at least one phospholipid (c) are present in a weight ratio of (a):((b)+(c)) ranging from 1:1.1 and 1:2.

In some embodiments, a proliposomal powder dispersion disclosed herein comprises (a) testosterone, (b) cholesterol, and (c) at least one phospholipid. In some embodiments, a proliposomal powder dispersion disclosed herein comprises (a) testosterone, (b) cholesterol, and (c) two phospholipids. The phospholipid component of a powder dispersion disclosed herein is any pharmaceutically acceptable phospholipid and mixtures of such phospholipids. Natural as well as synthetic phospholipids may be used. Phospholipids are molecules that have two primary regions, a hydrophilic head region comprised of a phosphate of an organic molecule and one or more hydrophobic fatty acid tails. Naturally-occurring phospholipids generally have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, known as a phospholipid bilayer or a lamella, converge into a liposome. In doing so, the liposomes (or phospholipid spheres) entrap some of the aqueous medium, and whatever may be dissolved or suspended in it, in the core of the sphere. This includes components of a proliposomal powder dispersion disclosed herein, such as testosterone and other components.

Examples of suitable phospholipids that may be used in a proliposomal powder dispersion disclosed herein include but are not limited to distearoyl phosphatidylcholine, dipalmitoyl phosphatidylcholine, dimyristoyl phosphatidylcholine, egg phosphatidylcholine, soy phosphatidylcholine, dimyristyl phosphatidyl glycerol sodium, 1,2-dimyristoyl-phosphatidic acid, dipalmitoylphosphatidylglycerol, dipalmitoyl phosphate, 1,2-distearoyl-sn-glycero-3-phospho-rac-glycerol, 1,2-distearoyl-sn-glycero-3-phosphatidic acid, phosphatidylserine and sphingomyelin. The proliposomal powder dispersions disclosed herein may also comprise individual combinations of any of the aforementioned phospholipids. In some embodiments, phospholipids containing saturated fatty acids are employed. In certain instances, use of phospholipids containing saturated fatty acids avoid stability (chemical) problems sometimes associated with unsaturated fatty acids. The phospholipid, distearoyl phosphatidylcholine, has been found to be particularly useful in the powder dispersions described herein. In some embodiments, the phospholipid is distearoyl phosphatidylcholine.

In some embodiments, a proliposomal powder dispersion disclosed herein comprises (a) testosterone, (b) cholesterol, and (c) at least one phospholipid. In some embodiments, a proliposomal powder dispersion disclosed herein comprises (a) testosterone, (b) a cholesterol derivative, and (c) at least one phospholipid. In some embodiments, a proliposomal powder dispersion disclosed herein comprises (a) testosterone, (b) cholesterol, a cholesterol derivative, or a combination thereof, and (c) at least one phospholipid, wherein the amount of a cholesterol derivative in the proliposomal dispersion corresponds to a molar amount of cholesterol allowed in a proliposomal dispersion based on the range of weight:weight ratios of cholesterol to the other proliposomal dispersion components that are specified herein. The cholesterol component of the proliposomal powder dispersion disclosed herein is either cholesterol (3β-hydroxy-5-cholestene 5-cholesten-3β-ol) or a cholesterol derivative. Examples of suitable cholesterol and derivatives include, but are not limited to: 22(R)-hydroxycholesterol; 22(S)-hydroxycholesterol; 25-hydroxycholesterol; 5-cholesten-3β-ol-7-one; 5α-cholest-7-en-3β-ol; 5α-cholestan-3β-ol; 5α-cholestane; 5β-cholestan-3α-ol; 7β-hydroxycholesterol; campesterol; cholesta-3,5-diene; cholestanol; cholesterol 5α,6α-epoxide; cholesterol 5β,6β-epoxide; cholesterol-PEG 600; cholesterol; cholesteryl 10-undecenoate; cholesteryl acetate; cholesteryl arachidonate; cholesteryl behenate; cholesteryl butyrate; cholesteryl caprylate; cholesteryl dodecanoate; cholesteryl elaidate; cholesteryl erucate; cholesteryl heptadecanoate; cholesteryl heptanoate; cholesteryl hexanoate; cholesteryl linoleate; cholesteryl linolelaidate; cholesteryl myristate; cholesteryl N-(trimethylammonio-ethyl)carbamate chloride; cholesteryl n-decanoate; cholesteryl n-valerate; cholesteryl nervonate; cholesteryl oleate; cholesteryl palmitate; cholesteryl palmitelaidate; cholesteryl pelargonate; cholesteryl phenylacetate; cholesteryl stearate; glycocholic acid hydrate; lanosterol; sodium cholesteryl sulfate; stigmastanol; SyntheChol®; Thiocholesterol. The proliposomal powder dispersions disclosed herein may also comprise individual combinations of any of the aforementioned cholesterol components.

In some embodiments, a proliposomal powder dispersion disclosed herein is prepared by first dissolving testosterone in a solvent. The solvent is any solvent in which testosterone dissolves, but is preferably a water-miscible solvent. Examples of such solvents include, but are not limited to, ethanol, methanol, chloroform, dichloromethane, acetone, isopropyl alcohol, and diethyl ether. If water is to be present in combination with a water-miscible solvent, (e.g., an ethanol and water solvent system), the water may be added before or after the testosterone is dissolved. Solvent-water systems are also made on a volume to volume basis, and the amount of water should not be so much that the phospholic forms liposomes. Generally, the solvent solution should not comprise 10% or more of water (vol/vol). Once the testosterone is dissolved, in some embodiments cholesterol, and at least one phospholipid, as well as any other proliposomal powder components are added to the solution and mixed to form a solution or dispersion of the components in the solvent. In various embodiments, the amounts of phospholipid and cholesterol added to the solution are such that the ratio (wt/wt) of testosterone to phospholipid to cholesterol ranges from (0.50-3.50):(0.50-3.00):(0.05-0.50). In various embodiments, the amounts of phospholipid and cholesterol added to the solution are such that the ratio (wt/wt) of testosterone to phospholipid to cholesterol range from (about 0.50-about 3.50):(about 0.50-about 3.00):(about 0.05-about 0.50). In some embodiments, the ratio (wt/wt) of testosterone to phospholipid to cholesterol ranges: (1.00:0.90:0.10); (1.50:1.35:0.15); (1.50:2.70:0.30); (1.00:1.35:0.15); or (3.00:2.70:0.30), respectively, as well as any ratio in between these ratios. In some embodiments, the ratio (wt/wt) of testosterone to phospholipid to cholesterol ranges: (about 1.00:about 0.90:about 0.10); (about 1.50:about 1.35:about 0.15); (about 1.50:about 2.70:about 0.30); (about 1.00:about 1.35:about 0.15); or (about 3.00:about 2.70:about 0.30), respectively, as well as any ratio in between these ratios. The dissolution of testosterone and the mixing of other components is done in one or a series of steps and by any suitable means and preferably by stirring. In some embodiments, after mixing, the solvent is removed to yield a powder. The solvent is removed by suitable technique, for example, by evaporation, by placing the solution under vacuum, by spray-drying, or by use of a drying gas, and the like. In some embodiments, the components are mixed by stirring at room temperature until the solvent evaporates, i.e., by stirring overnight. In some embodiments, a method of removing the solvent further comprises use of heat. The particle size of resulting powder dispersion may be reduced by grinding, passing the powder through screens, or by any other suitable technique. In some embodiments, the particles within a proliposomal powder dispersion described herein may have powder size ranging from about 10 to 200 mesh, 20 to 120 mesh or 40 to 80 mesh. If desired, the proliposomal powder dispersion may undergo further drying to remove or reduce the amount of any residual solvent still present in the powder. Such a further drying step is performed by using one or more of the drying techniques discussed above or by other suitable drying technique.

In some embodiments, a proliposomal powder dispersion disclosed herein further comprises other pharmaceutically acceptable excipients. When preparing a proliposomal powder dispersion described herein, excipients are generally added to the combined, powdered mixture of testosterone, cholesterol and phospholipid, i.e., excipients are added "externally." For example, the free-flowing powdered formulation may be admixed with at least one pharmaceutically acceptable excipient. Exemplary pharmaceutically acceptable excipients include, but are not limited to: (a) fillers or extenders, such as, for example, starches, lactose (e.g., lactose monohydrate), sucrose, glucose, mannitol, and silicic acid; (b) binders, such as, for example, cellulose derivatives, including microcrystalline cellulose, e.g., the various Avicel® PH products (FMC BioPolymer—Philadelphia, Pa.) (e.g., Avicel® PH-101 and PH-102), and Prosolv® SMCC 90 and Prosolv® SMCC 90 HD (JRS Pharma—Rosenberg, Germany), starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, e.g., sodium starch glycolate (e.g., Explotab® disintegrant (JRS Pharma—Rosenberg, Germany)), alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, (i) lubricants, such as, for example, talc, calcium stearate, magnesium stearate, solid polyethylene glycols, sodium lauryl sulfate (SLS), (j) plasticizers, and (k) dispersants, including mannitol, e.g., Pearlitol® SD 2000 (Roguette Pharma—Lestrem, France), or combinations thereof. In some embodiments, the pharmaceutically acceptable excipients are used in any suitable amount for the particular excipient. Where the excipient is not a binder, in some embodiments the excipients are present in a testosterone:excipient weight ratio ranging from about 1:about 0.05 to about 1:about 0.3, and from about 1:about 0.1 to about 1:about 0.2. Where the excipient is not a binder, in some embodiments the excipients are present in a testosterone: excipient weight ratio ranging from 1:0.05 to 1:0.3, and from about 1:0.1 to 1:0.2. Where the excipients are binders, in some embodiments the testosterone: excipient weight ratio ranges from about 1:about 0.5 to about 1:about 4. Where the excipients are binders, in some embodiments the testosterone: excipient weight ratio ranges from 1:0.5 to 1:4.

In some embodiments, a formulation described herein further comprises a disintegrating agent. In various embodiments, the formulation comprises the disintegrating agent, sodium starch glycolate, e.g., Explotab® disintegrant. Other suitable disintegrating agents may also be sued. In some embodiments, the ratio of disintegrating agent to the combined mixture of testosterone, phospholipid, and cholesterol ("the proliposomal powder component of the formulation") ranges from about 1:about 10 to about 1:about 35 (wt/wt), which correlates to a ratio of disintegrating agent to testosterone that ranges from about 1:about 5 to about 1:about 20. In some embodiments, the ratio of disintegrating agent to the combined mixture of testosterone, phospholipid, and cholesterol ("the proliposomal powder component of the formulation") ranges from 1:10 to 1:35 (wt/wt), which correlates to a ratio of disintegrating agent to testosterone that ranges from 1:5 to 1:20.

In some embodiments, a formulation described herein further comprises a binder. Because binders are often classified according to particle size, the particle size of the binder excipient that is included in the formulation is selected based on the knowledge and skill of one of skill in the pharmaceutical formulation arts. In some embodiments, the binder is a microcrystalline cellulose, such as Avicel®PH-101, which has a particle size of 50 µm, or Avicel® PH-102, which has a particle size of 100 µm. Alternatively, in other embodiments, the binder is Pros® Iv® SMCC 90 or Pros® Iv® SMCC 90 HD which are both microcrystalline cellulose binders, each with a particle size of 110 µm. In still other embodiments, the binder is dibasic calcium phosphate (DCP). In some embodiments, the ratio of microcrystalline cellulose binder to the proliposomal powder component of the formulation ranges from from 1:1 to 3:1 (wt/wt), which correlates to a ratio of binder to testosterone that ranges from 4:1 to 1.5:1. In some embodiments, the ratio of microcrystalline cellulose binder to the proliposomal powder component of the formulation ranges from about 1:about 1 to about 3:about 1 (wt/wt), which correlates to a ratio of binder to testosterone that ranges from 4:1 to 1.5:1. In some embodiments, the binder is DCP and the ratio of binder to the proliposomal powder component ranges from 0.25:1 to 1.6:1 wt/wt), which correlates to a ratio of binder to testosterone that ranges from 0.20:1 to 0.50:1. In some embodiments, the binder is DCP and the ratio of binder to the proliposomal powder component ranges from about 0.25:about 1 to about 1.6:about 1 wt/wt), which correlates to a ratio of binder to testosterone that ranges from about 0.20:about 1 to about 0.50:about 1.

In some embodiments, a formulation described herein further comprises a lubricant. In some embodiments, the formulation comprises the lubricant, magnesium (Mg) stearate. In some embodiments, the ratio of lubricant to the proliposomal powder component of the formulation ranges from 145:1 to 225:1 (wt/wt), which correlates to a ratio of lubricant to testosterone that ranges from 70:1 to 115:1. In some embodiments, the ratio of lubricant to the proliposomal powder component of the formulation ranges from about 145:about 1 to about 225:about 1 (wt/wt), which correlates to a ratio of lubricant to testosterone that ranges from about 70:about 1 to about 115:about 1.

In some embodiments, a formulation described herein further comprises a dispersant. In some embodiments, the formulation comprises the dispersant, mannitol, e.g., Pearlitol® SD 200. In some embodiments, the ratio of dispersant to the proliposomal powder component of the formulation ranges from 0.20:1 to 0.60:1 (wt/wt), which correlates to a ratio of dispersant to testosterone that ranges from 0.40:1.0 to 1.5:1.0. In some embodiments, the ratio of dispersant to the proliposomal powder component of the formulation ranges from about 0.20:about 1 to about 0.60:about 1 (wt/wt), which correlates to a ratio of dispersant to testosterone that ranges from about 0.40:about 1.0 to about 1.5:about 1.0.

Disclosed herein, in certain embodiments, is an oral dosage form comprising a proliposmal powder dispersion or a pharmaceutical composition described herein. Exemplary forms of the pharmaceutical compositions described herein, include, a tablet, a pill, a powder, a capsule (including both soft or hard capsules made from animal-derived gelatin or plant-derived HPMC), a sachet, a troche, pellets, granules, emulsions, and solutions. In some embodiments, the oral dosage form is a tablet or a capsule. In some embodiments, the oral dosage form has a delayed release coating (e.g., an enteric coating). In some embodiments, the oral dosage form has an enteric coating.

Tablets may be prepared by any suitable technique (e.g., compression techniques). Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., spray drying, pan coating, melt granulation, granulation, fluidized bed spray drying or coating (e.g., wurster coating), tangential coating, top spraying, tableting, extruding and the like.

Compressed tablets are solid dosage forms prepared by compacting the bulk blend formulations described above. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 5% of the tablet weight. In other embodiments, the compressed tablets include one or more excipients.

Provided herein are pharmaceutical compositions in film-coated dosage forms, which comprise a combination of an active ingredient, or a pharmaceutically acceptable salt, solvate, or prodrug thereof; and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating.

In some embodiments, compressed tablets are solid dosage forms prepared by compacting the bulk blend compositions described above. In some embodiments, the compressed tablets comprise a film surrounding the final compressed tablet.

Further provided herein are pharmaceutical compositions in enteric coated dosage forms, which comprise a combination of an active ingredient, or a pharmaceutically acceptable salt, solvate, or prodrug thereof; and one or more release controlling excipients for use in an enteric coated dosage form. The pharmaceutical compositions also comprise non-release controlling excipients. Enteric-coatings are coatings that resist the action of stomach acid but dissolve or disintegrate in the intestine.

Capsules include both soft and hard capsules, e.g., capsules made from animal-derived gelatin or plant-derived HPMC. In some embodiments, the capsule is a size 5, 4, 3, 2, 1, 0, 0E, 00, 000, 13, 12, 12el, 11, 10, 7 or Su07. In various embodiments, the capsule is a size '00' Vcaps or a hard gelatin capsule. In some embodiments, the capsules are filled with the powdered proliposmal testosterone formulation disclosed herein, including excipients.

In one embodiment, pharmaceutical compositions which are used orally include push-fit capsules made of gelatin, as well as soft, sealed capsules made of gelatin and a plasticizer, such as glycerol or sorbitol. In addition, in one embodiment, stabilizers are added.

Capsules are filled using any suitable techniques. A capsule may be prepared by placing the bulk blend composition, described above, inside a capsule.

It should be understood that many carriers and excipients may serve several functions, even within the same formulation.

As discussed above, the filled capsules may be coated with a delayed release coating (e.g., an enteric coating). In some embodiments, the delayed release coating (e.g., an enteric coating) releases the proliposmal powder dispersion in the small intestine. In various embodiments, the delayed release coating (e.g., an enteric coating) composition comprises a polymer, such as an aqueous dispersion of anionic polymers with methacrylic acid as a functional group (e.g., Eudragit® L30D-55 (Evonik Industries). In some embodiments, the delayed release coating (e.g., an enteric coating) composition comprises a plasticizer (e.g., triethyl citrate). In some embodiments, the delayed release coating (e.g., an enteric coating) composition comprises an anti-tacking agent (e.g., talc). In some embodiments, the delayed release coating (e.g., an enteric coating) composition comprises a diluent such as water. In some embodiments, the coating composition comprises about: about 42 weight % (wt %) of an aqueous dispersion of anionic polymers with methacrylic acid as a functional group; about 1.25 wt % of a plasticizer; about 6.25 wt % of an anti-tacking agent; and about 51 wt % of a diluent. In some embodiments, the coating composition comprises about: 42 weight % (wt %) of an aqueous dispersion of anionic polymers with methacrylic acid as a functional group; 1.25 wt % of a plasticizer; 6.25 wt % of an anti-tacking agent; and 51 wt % of a diluent. In some embodiments, for example when a large-scale preparations are preferred, an appropriate amount of an anionic copolymer based on methacrylic acid and ethyl acrylate, such as Eudragit® L100-55, is used in place of Eudragit® L30D-55. The coating composition is applied to the capsules by using any suitable method, such as, but not limited to using a Procept pan coating machine and Caleva mini coater air suspension coating machine to coat the capsules until they experience a 10% to 15% weight gain.

In some embodiments, the solid dosage forms described herein can be formulated as enteric coated delayed release oral dosage forms, i.e., as an oral dosage form of a pharmaceutical composition as described herein which utilizes a delayed release coating (e.g., an enteric coating) to affect release in the small intestine of the gastrointestinal tract.

In some embodiments, the solid dosage forms described herein are coated. In various embodiments contemplated herein, the coating is, for example, a gastric resistant coating such as an delayed release coating (e.g., an enteric coating), a controlled-release coating, an enzymatic-controlled coating, a film coating, a sustained-release coating, an immediate-release coating, a delayed-release coating, or a moisture barrier coating. See, e.g, *Remington's Pharmaceutical Sciences,* 20th Edition (2000).

In some embodiments a delayed release formulation is prepared by (a) spraying the proliposmal dispersion on to nonpareil beads by top spray configuration, (b) coating the beads with a barrier coat, and (c) coating the beads an delayed release coating (e.g., an enteric coating) polymer. The enteric coated nonpareil beads are then formulated as tablets or capsules.

The term "delayed release" as used herein refers to the delivery so that the release can be accomplished at some generally predictable location in the intestinal tract more distal to that which would have been accomplished if there had been no delayed release alterations. In some embodiments, the pharmaceutical compositions described herein release the testosterone in the small intestine. In some embodiments, the pharmaceutical compositions described herein release the testosterone in the duodenum, jejunum or ileum. In some embodiments, the pharmaceutical compositions described herein release the testosterone in the large intestine. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as a delayed release coating (e.g., an enteric coating) in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

(a) Shellac, also called purified lac, a refined product obtained from the resinous secretion of an insect. This coating dissolves in media of pH >7;

(b) Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit® series E, L, S, RL, RS and NE (Evonik industries) are available as solubilized in organic solvent, aqueous dispersion, or dry powders. The Eudragit® series RL, NE, and RS are insoluble in the gastrointestinal tract but are permeable and are used primarily for colonic targeting. The Eudragit® series E dissolve in the stomach. The Eudragit® series L, L-30D and S are insoluble in stomach and dissolve in the intestine;

(c) Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH >5, and it is much less permeable to water vapor and gastric fluids.

In some embodiments, the coating may contain a plasticizer and possibly other coating excipients such as colorants, talc, and/or magnesium stearate, which are well known in the art. Suitable plasticizers include triethyl citrate (Citroflex® 2), triacetin (glyceryl triacetate), acetyl triethyl citrate (Citroflec® A2), Carbowax® 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In some embodiments, a proliposomal powder dispersion disclosed herein improves the bioavailability of testosterone. In various embodiments, a fasting pharmacokinetic profile of mean plasma concentration of testosterone ranges from 300 ng/dL to 1050 ng/dL (including, 400 ng/dL to 950 ng/dL, 500 ng/dL to 950 ng/dL, and 600 ng/dL to 950 ng/dL) of testosterone five hours after administration under fasting conditions, i.e., ingestion of an oral dosage form described herein comprising 60 mg to 240 mg of testosterone. In some embodiments, a fasting pharmacokinetic profile of mean plasma concentration of testosterone is from about 300 ng/dL to about 1050 ng/dL of testosterone five hours after administration under fasting conditions, i.e., ingestion of an oral dosage form described herein comprising 60 mg to 240 mg of testosterone. In some embodiments, a fasting pharmacokinetic profile of mean plasma concentration of testosterone ranges from about 300 ng/dL to about 1050 ng/dL (including, about 400 ng/dL to about 950 ng/dL, about 500 ng/dL to about 950 ng/dL, and about 600 ng/dL to about 950 ng/dL) of testosterone five hours after administration under fasting conditions, i.e., ingestion of an oral dosage form described herein comprising from about 60 mg to about 240 mg of testosterone. In some embodiments, a fasting pharmacokinetic profile of mean plasma concentration of testosterone is about 350 ng/dL of testosterone five hours after administration under fasting conditions, i.e., ingestion of an oral dosage form described herein comprising about 100 mg to about 260 mg of testosterone. Such results represent as much as a 130 to 150 fold improvement in the mean plasma concentration of testosterone as compared to administration of equal dosages of unformulated testosterone. A dosage form described herein improves the bioavailability of testosterone under non-fasting, i.e., "fed" conditions. When a dosage form described herein is administered under fed conditions, the maximum plasma concentration ($C_{max}$) is about one half as much as the $C_{max}$ under fasting conditions five hours after administration. In some embodiments, the $C_{max}$ of the testosterone metabolite, dihydrotestosterone (DHT) is about 70 ng/dL after five hours. In some embodiments, the $C_{max}$ of the testosterone metabolite, dihydrotestosterone (DHT) is 70 ng/dL after five hours for a 120 mg dose. In some embodiments, after about 24 hours under fed conditions the plasma concentration of testosterone following the administration of a dosage form disclosed herein is greater than about 350 ng/dL, and the testosterone metabolite, DHT, has a $C_{max}$ of about 40 ng/dL, both of which are above a typical normal ranges of endogenous testosterone and DHT, respectively, in a human. In some embodiments, after 24 hours under fed conditions the plasma concentration of testosterone following the administration of a dosage form disclosed herein is 350 ng/dL, and the testosterone metabolite, DHT5 has a $C_{max}$ of 40 ng/dL, both of which are above a typical normal ranges of endogenous testosterone and DHT, respectively, in a human.

Dose Amounts

In certain embodiments, the amount of testosterone in the pharmaceutical compositions is about 5 mg to about 1.0 g per dose, 10 mg to about 1.0 g per dose, about 50 mg to about 500 mg per dose. In some embodiments, the amount of testosterone in the pharmaceutical compositions is about 5 mg per dose, 10 mg per dose, about 50 mg per dose, about 100 mg per dose, about 120 mg per dose, about 150 mg per dose, about 180 mg per dose, about 210 mg per dose, about 240 mg per dose, about 270 mg per dose, about 300 mg per dose, about 350 mg per dose, about 400 mg per dose, about 450 mg per dose, about 500 mg per dose, or about 1000 mg per dose. In some embodiments, the amount of testosterone in the pharmaceutical compositions is about 120 mg per dose. In some other embodiments, the amount of testosterone in the pharmaceutical compositions is about 240 mg per dose In general, doses employed for adult human treatment are typically in the range of 50 mg-1000 mg per day. In one aspect, doses employed for adult human treatment are from about 100 mg to about 300 mg per day. In some embodiments, doses employed for adult human treatment are about 120 mg per day. In some embodiments, doses employed for adult human treatment are about 240 mg per day. In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for testosterone is from about 0.01 to about 10 mg/kg per body weight. In other embodiments, the daily dosage or the amount of active in the dosage form are lower or higher than the ranges indicated herein.

Methods of Dosing and Treatment Regimens

In some embodiments, the proliposomal powder dispersions and the pharmaceutical compositions disclosed herein are administered to an individual in need of testosterone replacement therapy as often as testosterone replacement therapy is needed. In one embodiment, the pharmaceutical compositions described herein are administered for prophylactic and/or therapeutic treatments. In therapeutic applications, the compositions are administered to an individual already suffering from a disease or condition, in an amount sufficient to remove all symptoms or at least partially arrest at least one of the symptoms of the disease or condition. In certain embodiments, amounts effective for this use depend on the severity and course of the disease or condition, previous therapy, the individual's health status, weight, and response to the drugs, and/or the judgment of the treating physician.

In prophylactic applications, compositions described herein are administered to an individual susceptible to or otherwise at risk of a particular disease, disorder or condition. Such an amount is defined to be a "prophylactically effective amount or dose." In this use, the precise amounts also depend on the individual's state of health, weight, and the like. When used in an individual, effective amounts for this use will depend on the severity and course of the disease, disorder or condition, previous therapy, the patient's health status and response to the drugs, and the judgment of the treating physician.

In certain embodiments, administration of compositions or therapies as described herein includes chronic administration. In certain embodiments, chronic administration includes administration for an extended period of time, including, e.g., throughout the duration of the individual's life in order to ameliorate or otherwise control or limit the symptoms of the individual's disease or condition. In some embodiments, chronic administration includes daily administration.

In some embodiments, administration of the compositions or therapies described herein is given continuously. In alternative embodiments, the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-400%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the individual's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the individual requires intermittent treatment on a long-term basis upon any recurrence of symptoms.

The amount of testosterone that corresponds to such an amount varies depending upon factors such as the particular testosterone derivative, disease or condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

Combination Treatments

In certain instances, it is appropriate to administer the proliposomal powder dispersions and the pharmaceutical compositions disclosed herein with another therapeutic agent.

In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, the multiple therapeutic agents are administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the individual.

For combination therapies described herein, dosages of the co-administered therapeutic agents vary depending on the type of co-drug employed, on the specific drug employed, on the disease or condition being treated and so forth.

The individual therapeutic agents of such combinations are administered either sequentially or simultaneously in separate or combined pharmaceutical formulations. In one embodiment, the individual therapeutic agents will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

In some embodiments, the proliposomal powder dispersions and the pharmaceutical compositions disclosed herein are administered in combination with other therapeutic agents that reduce the severity of or eliminate the adverse effects associated with testosterone supplementation. In some embodiments, adverse effects of testosterone supplementation include acne and oily skin, increased hematocrit, exacerbation of sleep apnea and acceleration of pre-existing prostate cancer growth in individuals who have undergone androgen deprivation. Another adverse effect may be significant hair loss and/or thinning of the hair. Exogenous testosterone also causes suppression of spermatogenesis and can lead to infertility.

In some embodiments, the proliposomal powder dispersions and the pharmaceutical compositions disclosed herein are administered in combination with other therapeutic agents that modulate testosterone metabolism. In some embodiments, the other therapeutic agents reduce testosterone metabolism to dihydrotestosterone (DHT). In some embodiments, the other therapeutic agents reduce testosterone metabolism to estrogens (e.g. estradiol).

In some embodiments, the proliposomal powder dispersions and the pharmaceutical compositions disclosed herein are administered in combination with a synthetic 5-alpha-reductase inhibitor. 5-Alpha-reductase inhibitors locks DHT, a byproduct of testosterone in the body. 5-Alpha-reductase inhibitors include, but are not limited to, finasteride, alfatradiol, and dutasteride.

In some embodiments, the proliposomal powder dispersions and the pharmaceutical compositions disclosed herein are administered in combination with clomifene.

Gonadotropin and testosterone therapy is available in treatment of hypogonadism in men. The treatment strategy depends on the age of patient and the goals of therapy (restore of fertility and/or produce and maintain of virilization). The gonadototropins and GnRH are useful in spermatogenesis stimulation. In some embodiments, the proliposomal powder dispersions and the pharmaceutical compositions disclosed herein are administered in combination with gonadotropins and/or GnRH.

In some embodiments, the compositions and methods described herein are also used in conjunction with estrogen inhibitors, for example aromatase inhibitors. In some embodiments, the proliposomal powder dispersions and the pharmaceutical compositions disclosed herein are administered in combination with an aromatase inhibitor or combinations of aromatase inhibitors. Exemplary aromatase inhibitors include, but are not limited to, aminoglutethimide, testolactone, anastrozole, letrozole, exemestane, vorozole, formestan, fadrozole, 4-hydroxyandrostenedione, 1,4,6-Androstatrien-3,17-dione (ATD), and 4-Androstene-3,6,17-trione ("6-OXO").

In one embodiment, the compositions and methods described herein are also used in conjunction with other therapeutic reagents that are selected for their particular usefulness against the condition that is being treated. For example, the compositions disclosed herein may be administered in combination with insulin where the conditions is testosterone deficiency associated with diabetes; the composition may be administered in combination with calcium or an osteoporosis medication where the condition to be treated is testosterone deficiency associated with osteoporosis; the compositions may be administered in combination with an HIV/AIDS medication where the condition to be treated is testosterone deficiency associated with HIV/AIDS; the compositions may be administered in combination with an chemotherapy or radiation therapy where the condition to be treated is testosterone deficiency associated with cancer.

Exemplary osteoporosis medications include calcium, calcitonin, parathyroid hormone, recombinant parathyroid hormone (e.g., teriparatide), a RANKL inhibitor (e.g., denosumab), a bisphosphonate (e.g., etidronate, clodronate, tiludronate, pamidronate, neridronate, olpadronate, alendronate, ibandronate, risedronate, zoledronate).

Exemplary HIV/AIDS medications include abacavir; amprenavir; atazanavir; darunavir; delavirdine; didanosine; edurant; efavirenz; emtricitabine; enfuvirtide; etravirine; fosamprenavir; indinavir; lamivudine; lopinavir; maraviroc; nelfinavir; nevirapine; raltegravir; ritonavir; saquinavir; stavudine; tenofovir disoproxil fumarate (DF); tipranavir; zalcitabine; zidovudine.

Exemplary chemotherapeutics include nitrogen mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane; immunostimulants such as for example ancestim, filgrastim, lenograstim, molgramostim, pegfilgrastim, sargramostim; interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; immunosuppressants such as for example azathioprine, lenalidomide, methotrexate, thalidomide; adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

Kits/Articles of Manufacture

For use in the therapeutic methods of use described herein, kits/articles of manufacture are also described herein. Such kits include a carrier, package, or container that is optionally compartmentalized to receive one or more doses of a pharmaceutical composition of testosterone as described herein. The kits provided herein contain packaging materials. Packaging materials for use in packaging pharmaceutical products include, but are not limited to those described in e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by treatment with testosterone replacement therapy.

For example, the container(s) include the proliposomal powder dispersions and the pharmaceutical compositions disclosed herein alone or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

The following ingredients, formulations, processes and procedures for practicing the methods disclosed herein correspond to that described above. The procedures below describe with particularity illustrative, non-limiting embodiments of formulations that include testosterone and methods of uses thereof.

Comparative Example 1: Preparation of Testosterone DMPG Proliposomal Formulations Comparative Proliposomal Formulations ("PLF-C"), PLF-C1, PLF-C2, PLF-C3, and PLF-C4 contained testosterone and dimyristyl phosphatidyl glycerol sodium (DMPG). Table 1 lists the components and amounts of each used to make each of these formulations. For PLF-C1, 0.5 g of testosterone was dissolved in 3 ml of a 9:1 ethanol to water mixture (v/v), and 0.5 g of DMPG was added to this solution. The solution was then stirred at room temperature until complete evaporation of the solvent was achieved, typically overnight. The powder formulation obtained upon evaporation of the solvent was passed through an appropriate sieve, such as mesh #60. The sieved powder was then transferred to a glass vial and stored at room temperature while protected from light.

The preparations of PLF-C2 and PLF-C3 were like that of PLF-C1, except that for PLF-C2, 1.5 g of testosterone and 1.5 g of DMPG were dissolved in 20 ml of the 9:1 ethanol-water solution, and for PLF-C3, 0.5 g testosterone and 1 g DMPG were dissolved in 10 ml of the 9:1 ethanol-water solution.

Formulation PLF-C4 was also prepared in the same way as PLF-C1 was prepared, except that 0.5 g of testosterone, and 0.5 g of DMPG were dissolved in 12 ml of an 1:1:0.3 mixture (v/v) of chloroform, ethanol, and water, respectively.

The above formulations were each filled into size "00" hard gelatin capsules, and then tested for their dissolution. Only PLF-C1 capsules were enteric coated. Specifically, the PLF-C1 coating material was Eudragit® L 30 D-55. Coating of PLF-C1 capsules was performed by first preparing a dispersion of Eudragit® L 30 D-55. To this dispersion was added amount of triethyl citrate equivalent to 10% of Eudragit® polymer weight to enhance film formation. Each capsule was dipped into the dispersion and then air dried a total of four times. Some of the capsules from formulation PLF-C1 were not coated. These uncoated capsules were also used in dissolution testing along with enteric coated capsules.

TABLE 1

| Ingredients | PLF-C1 Qty | PLF-C2 Qty | PLF-C3 Qty | PLF-C4 Qty |
| --- | --- | --- | --- | --- |
| Testosterone | 0.50 g | 1.50 g | 0.50 g | 0.50 g |
| DMPG | 0.50 g | 1.50 g | 1.00 g | 0.50 g |
| Ethanol:Water (9:1) mixture | 3 ml | 20 ml | 10 ml | — |
| Chloroform-ethanol-water mixture (1:1:0.3) | — | — | — | 12 ml |
| Drug:Lipid Ratio | 1:1 | 1:1 | 1:2 | 1:1 |

Comparative Example 2: In Vitro Dissolution of Testosterone DMPG Proliposomal Formulations In vitro dissolution profiles of testosterone from enteric-coated and uncoated PLF-C1 capsules were obtained. For these studies, three different dissolution media were used for enteric coated capsules. The enteric coated capsules (n=3) were dissolved in 500 ml of either: 1) 0.1 N HCl (pH 1.20) for 1 h; sodium acetate buffer (pH 4.50) for 1 h; potassium phosphate buffer (pH 6.80) for 3 h. For uncoated capsules, (n=3), only 0.1N HCl (pH 1.20) was used and samples were collected after 1, 2 and 2.5 h. Dissolution was allowed to proceed in a USP type-1 apparatus at a speed of 50 rotations per minute (rpm) at 37° C. for 0.5 h, 1 h, 2 h, and 3 h. At each timepoint, 5 ml samples were collected. The amounts of testosterone that were released at each time point were determined by using the following high pressure liquid chromatography (HPLC) assay method to analyze each timepoint sample. For each formulation analyzed, an amount of the formulation that contains 25 mg of testosterone was dissolved in 25 ml of ethanol. This stock solution was further diluted suitably with a methanol: water (1:1) solution until the concentration of testosterone reached 10 µg/ml. A 20 µl aliquot was then injected into the HPLC. The composition of mobile phase used in the HPLC analysis was a solution of acetonitrile: (water with 0.2% formic acid) (75:25 v/v). Separation of the phases was achieved by using a C18 (100×4.6 mm; 5 µm) Kinetex, Phenomenex® column at a flow rate of 1.0 ml/min. The total run time for each sample was 5 min and the Photo Diode Array detector (PDA) detector was set at a wavelength of 243 nm. Both uncoated and coated capsule formulations showed a drug release of less than 3.46% in 3 hours in PBS pH 6.80. Enteric-coated capsules remained intact for 2 hours in acidic pH.

Figure 1:
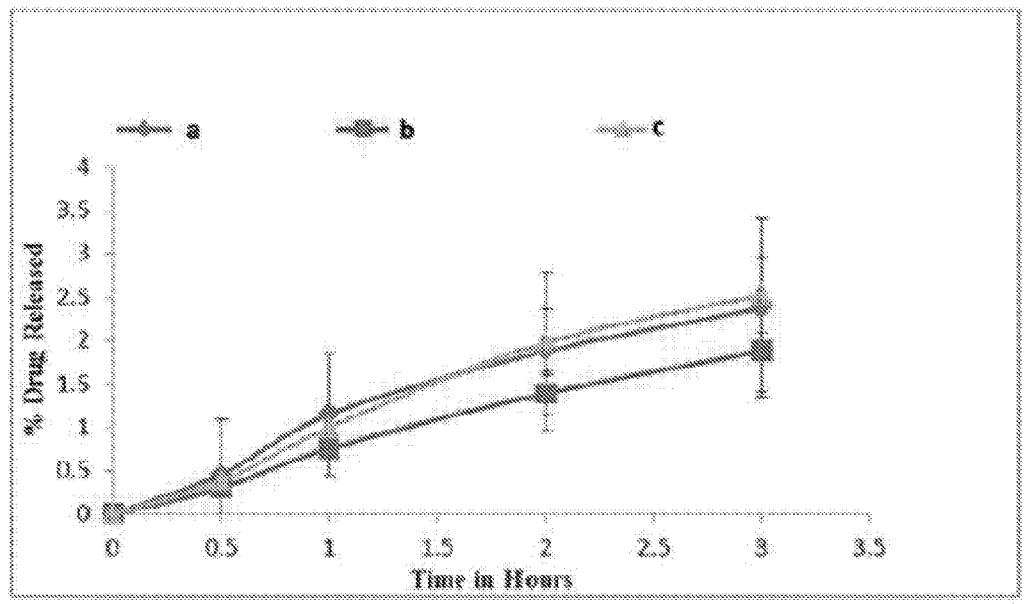
FIG. 1 exemplifies the in vitro testosterone dissolution profiles of encapsulated uncoated PLF-C2 that: (a) had not been stored; (b) stored for three months at room temperature; and (c) stored for three months at 30° C. See Comparative Example 2.
Figure 2:
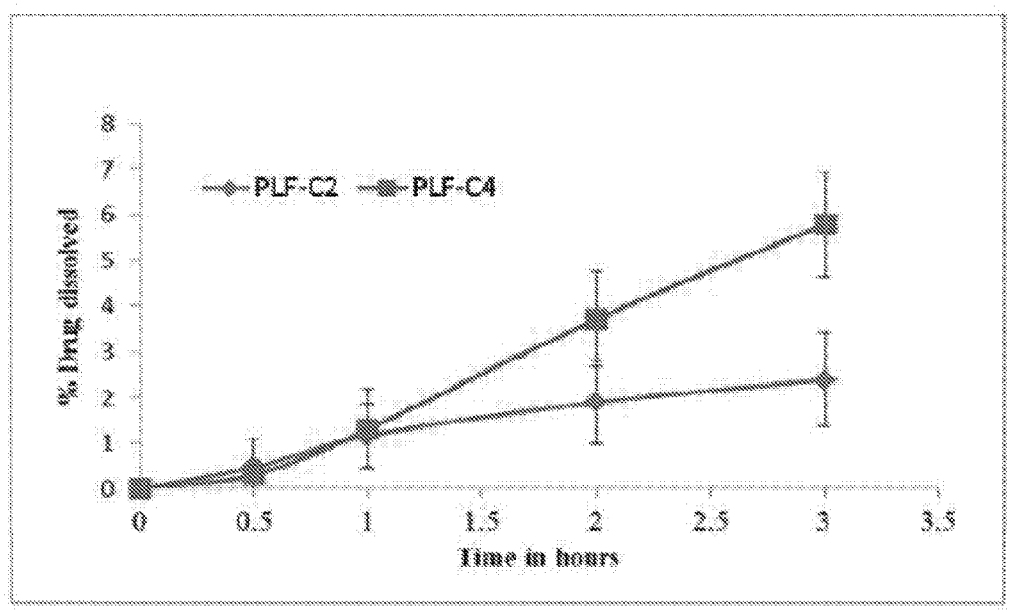
FIG. 2 exemplifies the in vitro release profiles of testosterone from uncoated capsules of PLF-C2 and PLF-C4 (which were prepared using different ratios of DPMG to the EtOH:water solvent solution) based on dissolution studies performed in PBS at pH 6.80. See Comparative Example 2.

In vitro dissolution profiles of testosterone from uncoated PLF-C2 capsules were also obtained. For these studies, uncoated capsules were dissolved in 900 ml of potassium phosphate buffer (pH 6.80). The dissolution and analysis parameters that were used were the same as described above for the PLF-C1 studies. The in vitro release profiles of testosterone from PLF-C2 uncoated capsules stored in screw-capped glass vials at different temperatures is shown in Table 2 and FIG. 1. The differences between the testosterone release profiles of PLF-C2 and PLF-C4 uncoated capsules, which both comprise DMPG in different ratios, are shown in FIG. 2.

TABLE 2

| Formulation | Storage Temp. | Time of storage (months) | % Assay | % Drug dissolved at each time point (hours) | | | |
| --- | --- | --- | --- | --- | --- | --- | --- |
| | | | | 0.5 | 1 | 2 | 3 |
| PLF-C2 (D:DMPG is 1:1) | | 0, Initial | 138.23 | 0.46 ± 0.64 | 1.15 ± 0.70 | 1.88 ± 0.91 | 2.38 ± 1.03 |
| | RT | 1 | 123.81 | — | — | — | — |
| | 30° C. | 1 | 118.02 | — | — | — | — |
| | RT | 2 | — | — | — | — | — |
| | 30° C. | 2 | 122.92 | — | — | — | — |
| | RT | 3 | 122.80 | 0.30 ± 0.03 | 0.76 ± 0.07 | 1.39 ± 0.26 | 1.88 ± 0.48 |
| | 30° C. | 3 | 137.72 | 0.38 ± 0.13 | 1.00 ± 0.23 | 1.98 ± 0.38 | 2.53 ± 0.43 |

Comparative Example 3: In Vivo Testing of Testosterone DMPG Proliposomal Formulations Formulations PLF-C1, PLF-C2, and PLF-C3 were tested for their in vivo performance following oral administration in rats (n=3). These studies used an institutional animal ethical committee (IACUC)-approved in vivo protocol involving male Sprague Dawley® rats (Charles Rivers—Wilmington, Mass.) weighing approximately 250 grams each were cannulated in the jugular vein and were used for the study. The PLF-C1 formulation in its free-flowing proliposomal powder form, and a testosterone control solution (a 0.5% (wt/vol) dispersion of testosterone in an HPMC suspension were tested in fed rats after oral administration.

The PLF-C1 and testosterone control solutions were prepared by dispersing them in a 0.5% (w/v) hydroxypropylmethyl cellulose (HPMC) suspension. Fed rats were administered 1 ml of pure drug solution (300 mg/Kg body weight dose) and 2.5 ml of PLF-C1 formulation (300 mg/Kg body weight dose) by oral gavage, respectively. Blood samples were collected at 0, 1, 2, 4, 8, 12, 24 hours of dosing. The samples were stored at 4° C. until centrifuged. Plasma portions of the blood samples were separated from blood by centrifugation at 12,000 rpm and 4° C. for 15 min using a Microfuge® 22R centrifuge (Beckman-Coulter). Plasma samples were stored at −20° C. until they were analyzed.

In vivo studies were also performed using the PLF-C2 and PLF-C3 formulations. These formulations were administered orally to male SD rats fasted overnight with free access to water. The animals were divided into two groups each comprising of 3 animals each. Formulation PLF-C2 was administered to one group while PLF-C3 was given to the other group.

To prepare PLF-C2 and PLF-C3 for administration, amounts of each sufficient to administer the experimental dose of 300 mg/kg of body weight to five rats was weighed and dispersed in 20 ml of water. Rats were administered 4 ml of the respective suspended formulations. Blood samples were collected at time 0 (before dosing), as well as at 1, 2, 4, 8, 12 and 24 hours after administration. The collected samples were stored in an ice-box until centrifuged at 12,000 rpm for 15 min. at 4° C. Plasma was separated and stored at −20° C. until it was analyzed. Detection of testosterone in the plasma samples was performed by using a validated liquid chromatography tandem mass spectrometry method (LC-MS/MS) as described below.

HPLC-eluted samples were prepared for MS analysis of testosterone and DHT concentrations. Briefly, the HPLC system used was a Shimadzu CLASS-VP® System. The mobile phase solutions were (A) 0.2% formic acid in water, and (B) 0.2% formic acid in acetonitrile. The column used in the analysis was a 2×10 mm Duragel® G C18 guard cartridge (Peeke Scientific—Novato, Calif.). The injection volume was 25 µl, the gradient was determined by going from a 5% to a 30% solution of buffer (B) in 0.5 minutes, followed by going from a 30% to a 55% solution of (B) in 2 minutes. The flow rate was 400 µl/min.

Internal standards, i.e., calibration standards, quality control (QC) samples and HPLC-eluted plasma samples were prepared for LC/MS/MS analysis by precipitating 50 µl of each sample with 2× volumes of ice cold Internal Standard Solution (acetonitrile containing 50 ng/ml of testosterone 16, 16, 17-$d_3$, $d_3$-testosterone). In addition to $d_3$-testosterone serving as an internal standard, dihydrotestosterone (DHT) was used as a QC standard. The precipitated samples were centrifuged at 6100×g for 30 minutes (or equivalent). Following centrifugation, 100 µl of each supernatant was transferred to an auto-sampler plate and placed on a heating block for 1 hour to partially evaporate the acetonitrile in the samples. MS analysis of the samples was then performed according to the following parameters.

The testosterone detection step of the analysis was performed by using an Applied Biosystems/MDS SCIEX API 3000®-equipped with a TurbolonSpray® (Applied Biosystems) electro spray interface (ESI) system The flow of liquid solvent from the analytical column entered the heated nebulizer interface of the MS/MS analyzer. The above-solvent/sample mixture was first converted to vapor in the heated tubing of the interface at 400° C. The analytes (testosterone, DHT, and [D3]-testosterone), contained in the nebulized solvent, were ionized and a positive charge added by the corona discharge needle of the interface, which applies a large voltage to the nebulized solvent/analyte mixture. The ions passed through the orifice of the instrument and entered the first quadrapole. Quadrapoles 1 and 3 (Q1 and Q3) were the mass filters, allowing selection of ions based on their mass to charge ratio (m/z). Quadrapole 2 (Q2) was the collision cell, where ions were fragmented by collision with argon molecules.

Figure 3:
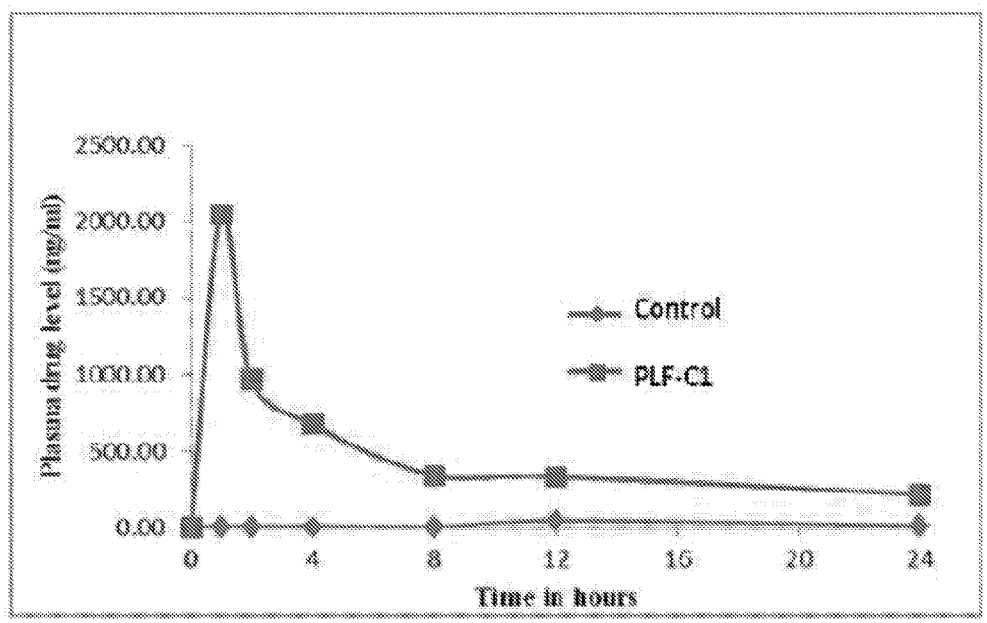
FIG. 3 exemplifies the mean plasma testosterone concentrations over time following oral administration of a suspension of PLF-C1 and an unformulated control testosterone suspension to non-fasted rats. See Comparative Example 3.
Figure 4:
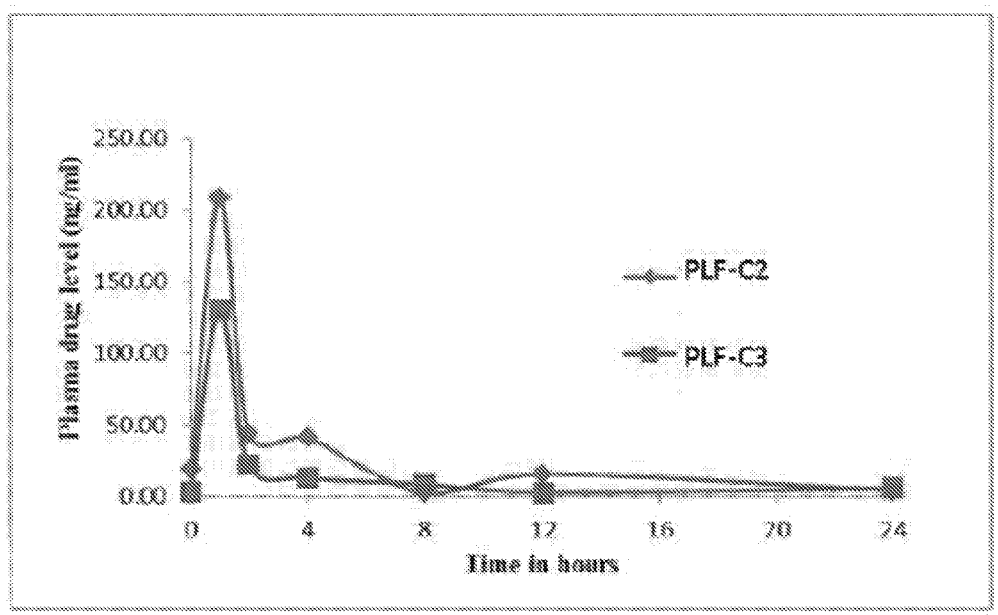
FIG. 4 exemplifies the mean plasma testosterone concentrations over time following oral administrations of a suspension of PLF-C2 and a suspension of PLF-C3 to fasted rats. See Comparative Example 3.

The first quadrapole of the MS/MS (Q1) selected for testosterone with an m/z value of 289.2, DHT with an m/z value of 291.2, or the internal standard, $d_3$-testosterone, with an m/z value of 292.2. Ions with these m/z values passed to the collision chamber (Q2), while ions with any other m/z collided with the sides of the quadrapole and were destroyed. Ions entering Q2 collided with neutral gas molecules. This process is called Collision-Induced Dissociation (CID). The CID gas used in this example was argon. The daughter ions generated were passed into quadrapole 3 (Q3), where the daughter ions of testosterone with an m/z value of 96.9, DHT with an m/z value of 255.2, or those of testosterone 16, 16, 17-$d_3$ ($d_3$-testosterone), the internal standard, with an m/z value of 96.9 were selected for, while other ions were screened out. The selected daughter ions were collected by the detector. Quantification is based on peak area ratio of analytes, i.e., testosterone, over the internal standard acquired by selective reaction monitoring (SRM) in positive mode. The mean plasma concentration over time profiles of the PLF-C1 formulation and testosterone control solution under fed conditions are shown in FIG. 3. The mean plasma concentration over time profiles of the PLF-C2 and PLF-C3 formulations under fasting conditions are shown in FIG. 4.

Comparative Example 4: Dissolution of DMPG-Based Formulations with Avicel PH101 and Lactose Monohydrate For formulation PLF-05, testosterone was dissolved in a mixture of ethanol:water (9:1). To this solution dimyristyl phosphatidyl glycerol sodium (DMPG) and lactose monohydrate were added and stirred overnight until complete evaporation of the solvent at room temperature. Lactose was added so that it helps in dispersion and avoids lump formation while preparing the dosing solution for animal studies.

Another formulation (PLF-05+Avicel® PH101) was prepared by adding Avicel® PH101 externally to the formulation (PLF-05) containing drug:DMPG:lactose (1:1:1). This approach was followed to see if Avicel® PH101 helps in increasing the dispersability of the formulation during dissolution.

In yet another example, formulation (PLF-05+Avicel® PH101+Explotab® disintegrant) was prepared by adding Avicel® and Explotab® disintegrant (1%) externally to PLF-05. This formulation was prepared with the objective of increasing the dispersion and there by the dissolution of the proliposomal formulation with the help of super disintegrating agent, Explotab® disintegrant and better dispersability of Avicel® PH101.

In yet another example, formulation PLF-C2 containing testosterone:DMPG in 1:1 ratio was taken and dispersed in 5 ml dissolution media first and then dissolution was performed. This was done to compare the dissolution of encapsulated PLF-C2 to dispersed PLF-C2 because, prior to animal dosing, the formulation was dispersed in water.

In yet another example, formulation PLF-C6 was prepared by dissolving testosterone in a mixture of ethanol:water (9:1). To the resulting testosterone solution, DMPG and Avicel® PH 101 were added at a ratio of 1:1:2, and dispersed by stirring the mixture overnight until the complete evaporation of the solvent had occurred at room temperature to form a proliposomal powder. To the dried proliposomal formulation, Explotab® disintegrant was added externally and the powder-Explotab® disintegrant mixture was formulated as a capsule. The objective was to see the effect of using dispersed Avicel® PH101 on dissolution of proliposomal formulation.

A testosterone proliposomal formulation was lyophilized. Specifically, formulation PLF-05 (500 mg) containing testosterone:DMPG:lactose (1:1:1) was taken and dispersed in 20 ml of water. It was hydrated at 40° C. for 30 min, and then lyophilized for more than 24 hours. The compositions of the variations of PLF-05 that were created by adding various excipients used are listed in Table 3.

In vitro dissolution studies of PLF-05 and PLF-05 formulations comprising additional excipients was carried out by using apparatus type I at 50 rpm. The dissolution media used was 900 ml of phosphate buffer (pH 6.80) that was maintained at 37±0.5° C. Samples (5 ml) were collected after 1, 2, 3 and 4 hours of dissolution. A type II apparatus was used for the dissolution of all other formulations in Table 3. All other dissolution parameters were same as that of PLF-05, described above.

Figure 5:
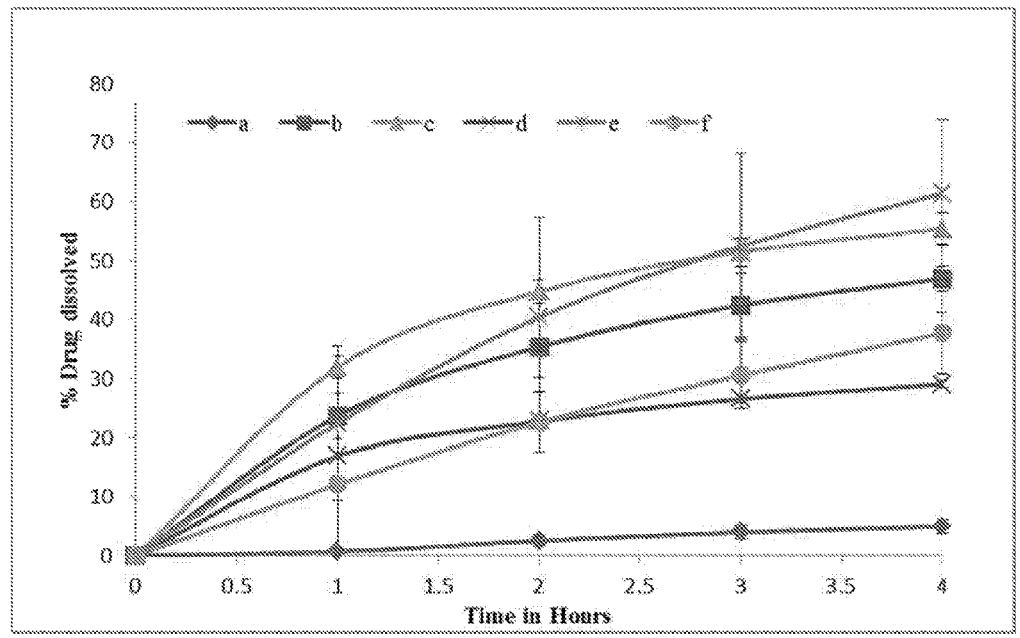
FIG. 5 exemplifies the in vitro testosterone dissolution profiles of: (a) PLF-05; (b) PLF-05 with Avicel® PH101; (c) PLF-05 with Avicel® PH101 and Explotab® disintegrant; (d) hydrated PLF-C2; (e) PLF-C6; and (f) lyophilized PLF-05. See Comparative Example 4 and Table 3.
Figure 6:
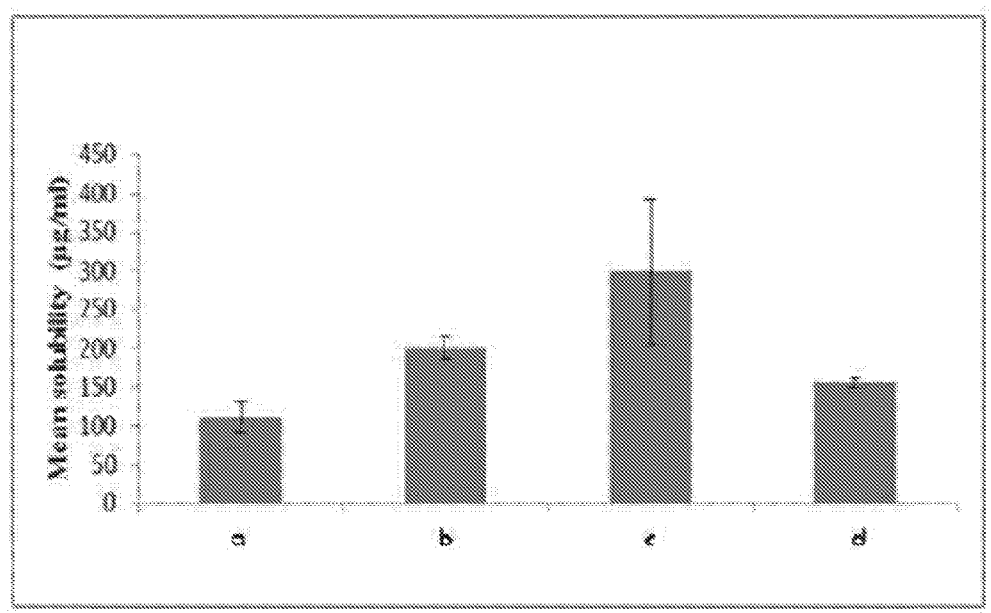
FIG. 6 exemplifies solubility of testosterone after 72 hours in: (a) HCl buffer pH 1.2; (b) Acetate buffer pH 4.5; (c) Phosphate buffer pH 6.8; and (d) Phosphate buffer 7.4. See Example 1.

Testosterone dissolution assays of the foregoing PLF-05 formulations were tested as per the method described in Comparative Example 2. The in vitro release profile of all the DMPG formulations described in Comparative Example 4 are shown in FIG. 5. As shown in FIG. 5, formulations containing Avicel® and Explotab® disintegrant gave higher release as compared to others.

buffer solution (PBS) pH 6.80 and d) nano pure water. These samples were subjected for shaking in a water bath for 72 h at RT. The samples were suitably diluted and analyzed by the HPLC assay method described in Comparative Example 2. Solubility of testosterone was high in phosphate buffer pH 6.80. See FIG. 6.

The solubility of testosterone was measured in the presence of lipid components at 37° C. in aqueous medium (pH 6.8) under the in vitro dissolution conditions described in Comparative Example 2. Physical mix formulations were prepared by mixing the dry components as per the compositions given in Table 4 (F1-F9). Dissolution parameters used for these studies are listed below. Samples collected at each time point were diluted suitably and analyzed by the HPLC assay method given in Comparative Example 2.

Figure 7:
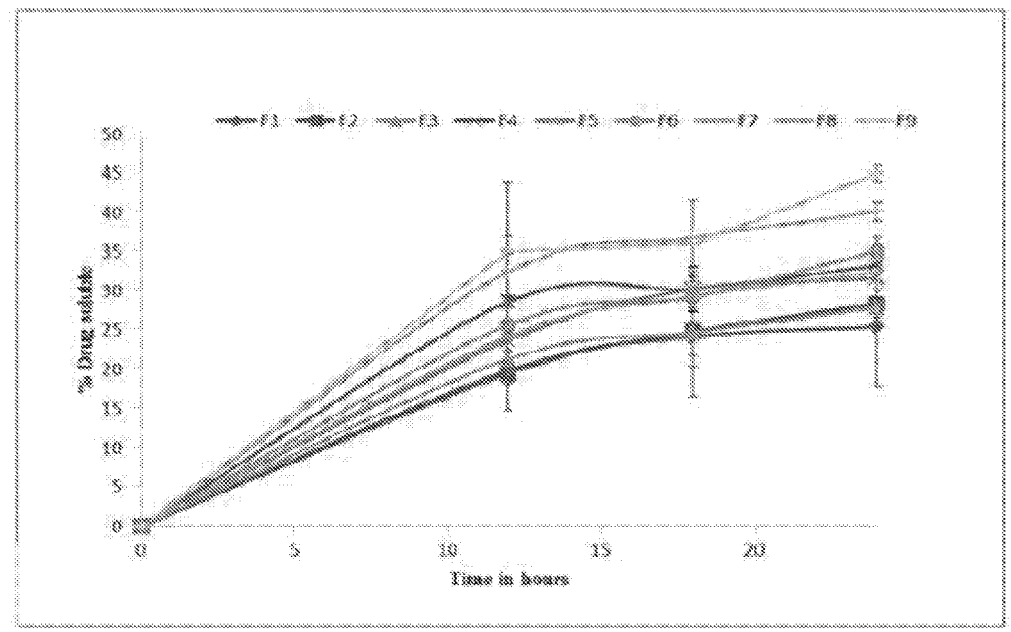
FIG. 7 exemplifies testosterone (T) solubilities following the dissolution of the following encapsulated formulations in PBS pH 6.80 at 37° C.: F1 (60% T, 32% DSPC, and 8% Cholesterol); F2 (60% T, 36% DSPC, and 4% Cholesterol); F3 (60% T, 40% DSPC, and 0% Cholesterol); F4 (50% T, 40% DSPC, and 10% Cholesterol); F5 (50% T, 45% DSPC, and 5% Cholesterol); F6 (50% T, 50% DSPC, and 0% Cholesterol); F7 (40% T, 48% DSPC, and 12% Cholesterol); F8 (40% T, 54% DSPC, and 9% Cholesterol); and F9 (40% T, 60% DSPC, and 0% Cholesterol). See Example 1 and Table 4.

The dissolution parameters for these dissolution studies were as follows. Formulations were dissolved using an USP Type 2 (Paddle) apparatus in a volume of 1000 ml of potassium phosphate buffer pH 6.80 (USP 30). Dissolution occurred at 37° C., and at 75 rpm. Samples (5 ml) were taken for analysis at 3, 5, 8 10, 12, 18 and 24 hours. The dissolution curve is shown in FIG. 7. Formulations F7 and F9 with maximum amount of DSPC in the range of 48% to 60% (w/w) showed high solubility in PBS (pH 6.80). See FIG. 7.

TABLE 4

| Formulation | Testosterone | | DSPC | | Cholesterol | |
| --- | --- | --- | --- | --- | --- | --- |
| | Wt % | mg/cap | Wt % | mg/cap | Wt % | mg/cap |
| F1 | 60 | 144.00 | 32 | 76.8 | 8 | 19.20 |
| F2 | 60 | 144.00 | 36 | 86.4 | 4 | 9.60 |
| F3 | 60 | 144.00 | 40 | 96.0 | 0 | 0 |
| F4 | 50 | 120.0 | 40 | 96.0 | 10 | 24.0 |
| F5 | 50 | 120.0 | 45 | 108.0 | 5 | 12.00 |
| F6 | 50 | 120.0 | 50 | 120.0 | 0 | 0 |
| F7 | 40 | 96.00 | 48 | 115.20 | 12 | 28.80 |
| F8 | 40 | 96.00 | 54 | 129.60 | 9 | 21.60 |
| F9 | 40 | 96.00 | 60 | 144.00 | 0 | 0 |

Example 2: Preparation of Testosterone/Cholesterol DSPC Proliposomal Formulations Proliposomal Formulation (PLF)-1, PLF-2, PLF-3, and PLF-4 were prepared by dissolving testosterone in a 9:1

TABLE 3

| Ingredients | (a) PLF-C5 | (b) | (c) | (d) PLF-C2 hydrated | (e) PLF-C6 | (f) Lyophilized |
| --- | --- | --- | --- | --- | --- | --- |
| Testosterone | 1.0 g | 0.10 g | 300 mg | 50 mg | 1.0 g | 0.50 g |
| DMPG (NOF Corp. Japan) | 1.0 g | (PLF-C5) | | 50 mg | 1.0 g | |
| Lactose monohydrate | 1.0 g | — | — | — | — | — |
| Avicel PH 101 | — | 0.10 g | 600 mg | — | 1.0 g | — |
| Explotab | — | — | 9 mg | — | 0.01 g | — |
| Ethanol:Water (9:1) mixture | 25 ml | 20 ml | — | — | — | — |
| Dissolution media | — | — | — | 5 ml | — | — |
| Water | — | — | — | — | — | 20 ml |

Example 1: Solubility Studies in Various Buffers

The solubility of testosterone in different media was tested. An amount of testosterone (100 mg) was added to each of four glass vials containing 10 ml of either: a) HCl buffer (pH 1.20), b) Acetate buffer (pH 4.50), c) phosphate mixture (v/v) of ethanol and water, followed by the addition of distearoyl phosphatidylcholine (DSPC) and cholesterol at a 9:1 ratio of DSPC to cholesterol (w/w). The resulting dispersion was stirred overnight until complete evaporation of the solvent at room temperature. The composition of these formulations is detailed in Table 5. The powder obtained upon removal of the solvent was passed through an appropriate sieve (mesh #60), transferred to a glass bottle, and stored at room temperature protected from light.

TABLE 5

| Ingredients | PLF-1 | PLF-2 | PLF-3 | PLF-4 |
|---|---|---|---|---|
| Testosterone | 1.00 g | 1.50 g | 1.50 g | 1.0 g |
| DSPC | 0.90 g | 1.35 g | 2.70 g | 1.350 g |
| Cholesterol | 0.10 g | 0.150 g | 0.30 g | 0.150 g |
| Ethanol:Water (9:1) mixture | 20 ml | 20 ml | 20 ml | 20 ml |
| Drug:Lipid ratio Lipid (DSPC + Cholesterol) | 1:1 | 1:1 | 1:2 | 1:1.5 |

Example 3: Solubility Studies

Figure 8:
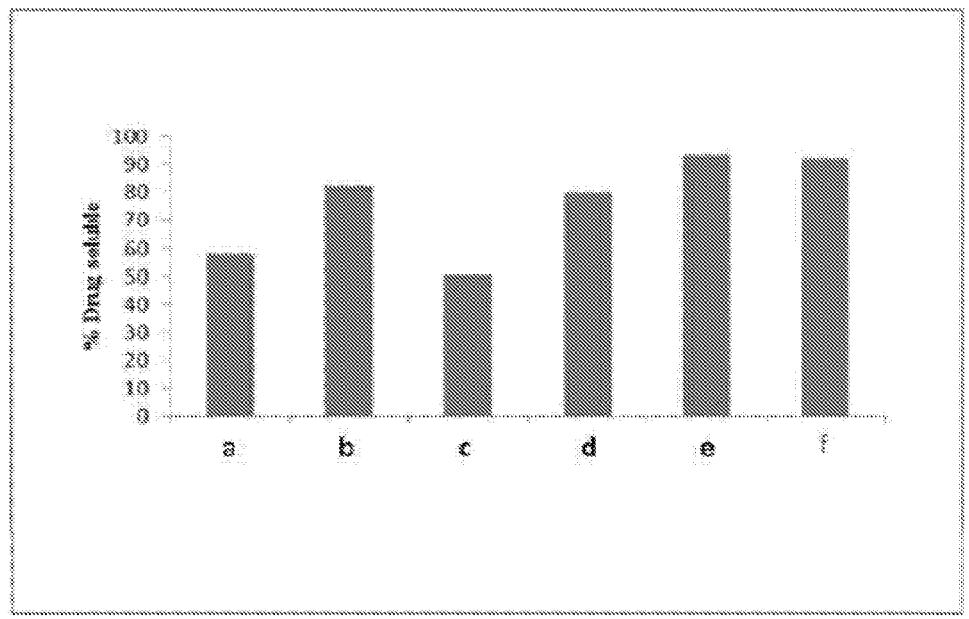
FIG. 8 exemplifies testosterone solubilities following the dissolution of: (a) unformulated testosterone in 0.5% SLS; (b) unformulated testosterone in 1% SLS; (c) unformulated testosterone in 2% SLS; (d) PLF-2 in 0.5% SLS; (e) PLF-2 in 1% SLS; and (f) PLF-2 in 2% SLS. See Example 3.

Solubility of: a) 10 mg pure testosterone; and b) formulation PLF-2 equivalent to 10 mg testosterone in either 0.5%, 1%, or 2% SLS following sonication for 10 min. was determined. For these studies, 10 mg of pure testosterone was weighed and dissolved in either 100 ml of 0.5%, 1%, or 2% (w/v) SLS, respectively, in volumetric flasks. An amount of formulation PLF-2 that contained 10 mg of testosterone was weighed, and sample solutions were prepared in a similar way as that described above for the testosterone control. These solutions were subjected for sonication for 10 min in a bath sonicator. The samples were then filtered and diluted suitably in their respective concentrations of SLS. The amounts of soluble testosterone for each concentration of SLS was determined by using the HPLC assay method described in Comparative Example 2. Both the testosterone control and PLF-2 were associated with high testosterone solubility in 1% w/v SLS. See FIG. 8.

Figure 9:
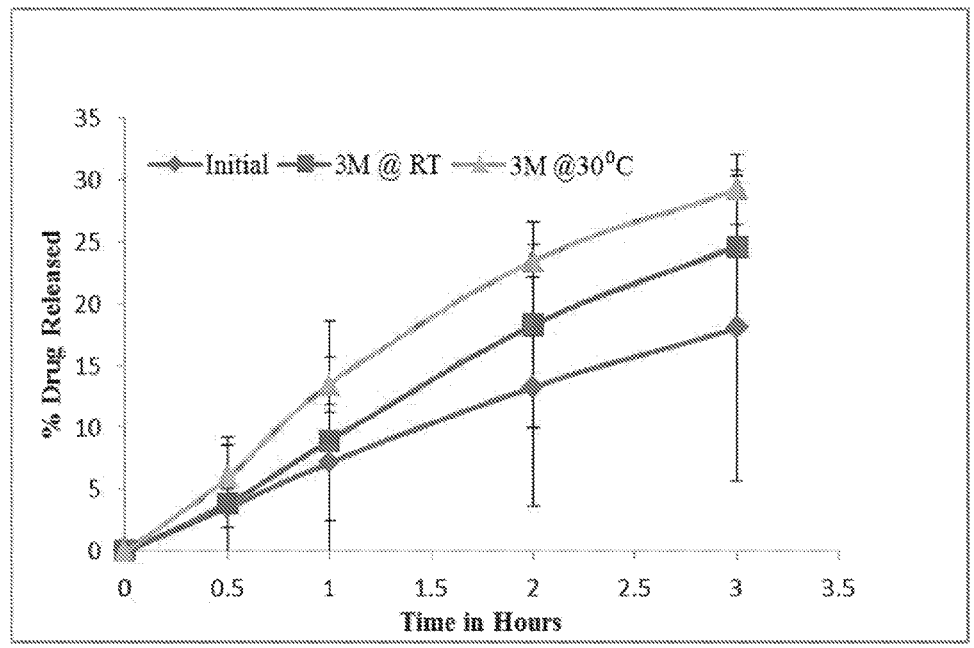
FIG. 9 exemplifies the in vitro testosterone dissolution profiles of encapsulated and enterically-coated PLF-1 that: (a) had not been stored; (b) stored for three months at room temperature; or (c) stored for three months at 30° C. See Example 4.

Example 4: In Vitro Dissolution Studies of Testosterone/Cholesterol DSPC Proliposomal Formulations Formulation PLF-1 was filled into size "00" hard gelatin capsules. Some of these capsules enterically coated as described in Comparative Example 2. Dissolution of both enteric-coated (n=3) and uncoated capsules (n=3) was carried out in 900 ml of potassium phosphate buffer (pH 6.80), and dissolution conditions were maintained throughout a three hour time course at 37±0.5° C. Samples (5 ml) were collected after 0.5, 1, 2 and 3 hours of dissolution, and then assayed according to the HPLC assay method as described above in Comparative Example 2. The stability data of PLF-1 is summarized in Table 6 and the in vitro release profile is given in FIG. 9.

Example 5: In Vivo Testing of Testosterone/Cholesterol DSPC Proliposomal Formulations The formulations PLF-2 and PLF-4 were prepared according to the method of their preparation described in Example 2. The formulations were then administered orally to male Sprague Dawley® (SD) rats after an overnight fast. Formulation PLF-2 was tested at 300 mg/kg, 150 mg/kg, 31 mg/kg, 15.5 mg/kg and 7.75 mg/kg doses of testosterone to body weight. Formulation PLF-4 was administered orally in a dose of 300 mg/kg body weight.

Figure 10:
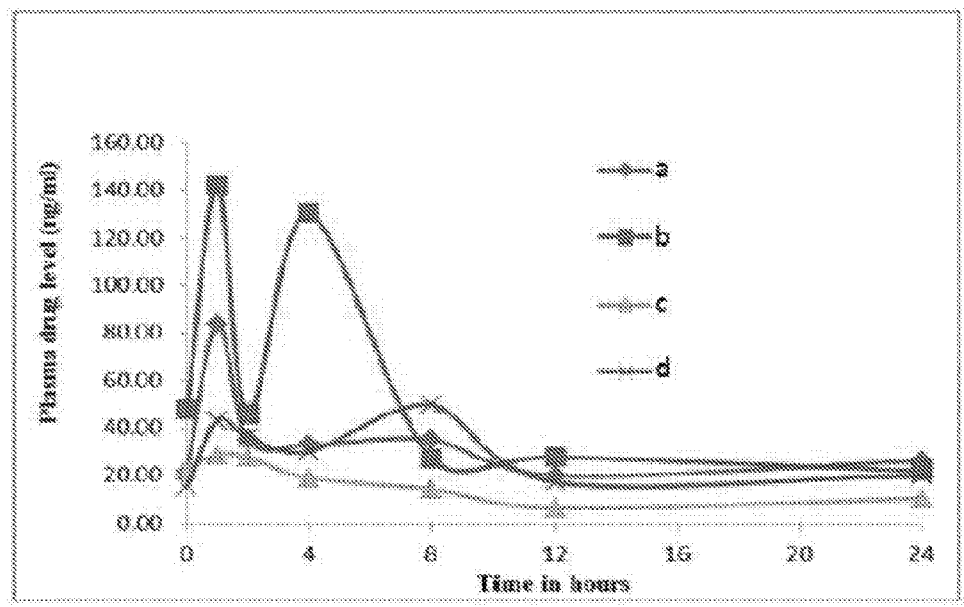

Male SD rats, which were cannulated in the jugular vein and weighed approximately 250 grams were used for the study. Animals were fasted overnight with free access to water. Sampling and analysis was followed as per the method described in comparative Example 4. The mean plasma concentration vs time profiles of the formulations that were tested are shown in FIGS. 10 and 11. The plasma concentrations of testosterone following the oral administration of different test formulations and a control testosterone dispersion were followed over time. Both 300 mg/Kg and 31 mg/Kg (testosterone dose/body weight) control and test formulations were studied.

Example 6: Dissolution of Testosterone/Cholesterol DSPC Proliposomal Formulations that Comprise Avicel® PH 101, Lactose Monohydrate, Magnesium Stearate A base Formulation called PLF-5 was prepared by dissolving 1.5 mg of testosterone in 20 ml of a 9:1 mixture (v/v) of ethanol and water, followed by the addition of 1.35 mg of distearoyl phosphatidylcholine (DSPC) and 0.15 mg of cholesterol, (i.e., a 9:1 ratio of DSPC to cholesterol (w/w)). The resulting dispersion was stirred overnight until complete evaporation of the solvent at room temperature. The powder obtained upon removal of the solvent was passed through an appropriate sieve (mesh #60), transferred to a glass bottle, and stored at room temperature protected from light. The PLF-5 formulation was then further formulated into PLF-5 formulations (a-d), as shown in Table 7, and described below.

PLF-5 (a) was prepared in capsule form, and was made with the objective of determining whether Avicel® PH101 and Explotab® disintegrant would increase the dispersability of the formulation during dissolution. PLF-5 (a) was prepared by the external addition (i.e., mixing the excipients and blending them with the Testosterone/Cholesterol DSPC Proliposomal Formulations) of the following ingredients to PLF-5: Avicel® PH 101 at a ratio of 1:2 (w/w); and

TABLE 6

| Formulation stored in glass vial | Storage Condition | Storage Time (Months) | % Assay | % Drug dissolved at time points | | | |
|---|---|---|---|---|---|---|---|
| | | | | 0.5 h | 1 h | 2 h | 3 h |
| PLF-1 D:DSPC:CH (1:0.9:0.1) | | Initial | 90.50 | 3.54 ± 1.54 | 7.15 ± 4.66 | 13.25 ± 9.59 | 18.01 ± 12.34 |
| | RT | 1 | 94.03 | — | — | — | — |
| | 30° C. | 1 | 99.17 | — | — | — | — |
| | RT | 2 | — | — | — | — | — |
| | 30° C. | 2 | 110.33 | — | — | — | — |
| | RT | 3 | 91.40 | 3.86 ± 5.39 | 8.92 ± 9.65 | 18.27 ± 8.29 | 24.58 ± 6.11 |
| | 30° C. | 3 | 101.06 | 5.97 ± 2.60 | 13.49 ± 2.24 | 23.41 ± 1.29 | 29.17 ± 2.78 |

Explotab® in the amount of 1% (w/w). The formulation mixture was then filled into capsules.

PLF-5 (b) was prepared in tablet form, and was made with the objective of determining whether the addition of Avicel® PH101, Explotab®, magnesium (Mg) stearate, and spray-dried lactose monohydrate would increase the dispersability of the formulation during dissolution. PLF-5 (b) was prepared by the external addition of the following ingredients to PLF-5: Avicel® PH 101 at a ratio of 1:2 (w/w); Explotab® in the amount of 1% (w/w); Spray-dried lactose monohydrate in an amount equivalent to 0.04 g per tablet; and Mg stearate in an amount equivalent to 8.75 mg per tablet. The mixture was formulated into an 8.9 mm circular biconvex tablet weighing 350 mg.

PLF-5 (c), which contained twice the amount of PLF-5 per dose, than PLF-5 (a) and (b) formulations, was prepared by the external addition of the following ingredients to PLF-5: Avicel® PH 101 at a ratio of 1.5:1 (w/w); Explotab® in the amount of 5% (w/w); and Mg stearate in an amount equivalent to 0.00875 g per tablet. The mixture was formulated into an 8.9 mm circular biconvex tablet weighing 350 mg.

PLF (d) was prepared exactly as PLF (c), but it was not tableted.

The in vitro testosterone dissolution profiles for the formulations PLF-5 (a-d) are provided in FIG. 12. Formulations containing Avicel® along with Explotab® disintegrant showed better dissolution profiles. In addition, both 1 wt % and 5 wt % Explotab® disintegrant-containing formulations showed similar release profiles.

The profiles were determined by using a type II apparatus at 50 rpm in 900 ml of PBS (pH 6.80) to dissolve the formulations. Samples were collected after 1, 2, 3 and 4 hours of dissolution, and were analyzed by the HPLC assay method described in Comparative Example 2.

TABLE 7

| Ingredients | PLF-5 (a) Capsule | PLF-5 (b) Tablet | PLF-5 (c) Tablet | PLF-5 (d) Powder |
|---|---|---|---|---|
| PLF-5 | | | | |
| 1.5 g Testosterone | 100 mg | 100 mg | 200 mg | 200 mg |
| 1.35 g DSPC | | | | |
| 0.15 g Cholesterol | | | | |
| Lactose monohydrate spray dried (SD) | — | 45 mg | — | — |
| Avicel ® PH 101 | 200 mg | 200 mg | 131 mg | 131 mg |
| Explotab ® | 3 mg | 3.5 mg | 17.5 mg | 17.5 mg |
| Magnesium stearate | — | 8.75 mg | 8.75 mg | 8.75 mg |

Example 7: Dissolution of Testosterone/Cholesterol DSPC Proliposomal Formulations that Comprise Avicel® PH 101/102, Lactose Monohydrate, Mg Stearate, and Pearlitol® 200 SD A base Formulation called PLF-6 was prepared by dissolving 3 mg of testosterone in 40 ml of a 9:1 mixture (v/v) of ethanol and water, followed by the addition of 2.7 mg DSPC and 0.30 mg of cholesterol, (i.e., a 9:1 ratio of DSPC to cholesterol (w/w)). The resulting dispersion was stirred overnight until complete evaporation of the solvent at room temperature. The powder obtained upon removal of the solvent was passed through an appropriate sieve (mesh #60).

A second, base formulation called PLF-7 was also prepared for these studies by dissolving 1.2 mg of testosterone in 30 ml of a 9:1 mixture (v/v) of ethanol and water, followed by the addition of 1.08 mg DSPC and 0.12 mg of cholesterol, (i.e., a 9:1 ratio of DSPC to cholesterol (w/w)). The resulting dispersion was stirred overnight until complete evaporation of the solvent at room temperature. The powder obtained upon removal of the solvent was passed through an appropriate sieve (mesh #60).

PLF-6 and PLF-7 were further formulated into PLF-6 formulations (a-c) and PLF-7 formulations (d-e), respectively, by the external addition of the respective amounts of Avicel® PH 101 or 102, Explotab®, Mg stearate, Pearlitol® 200 SD, reported in Table 8.

PLF-6 (a-c) and PLF-7 (d-e) were compressed into circular, biconvex 650 mg tablets. A ten-station rotary compression machine (Riddhi Pharma machinery Ltd., Ahmedabad, India) was used for preparing the tablets by direct compression. Avicel® PH 102 was used as an excipient for direct compression. Mannitol (Pearlitol® SD 200) was used with the intent of increasing tablet dispersion and thereby dissolution. The dissolution profiles of the tablets were compared with that of capsule formulations.

The in vitro dissolutions of PLF-6 (a-c) and PLF-7 (d) were carried out using type II apparatus at 50 rpm in 900 ml of PBS pH 6.80. However, the dissolution of PLF-7 (e) was carried out at 75 rpm. Samples were collected at the time intervals reported in FIG. 13 to analyze the release of testosterone from the formulations. The analyses were performed according to the HPLC assay method described in Comparative Example 2.

The comparison of formulations that contained either Avicel® PH 101 or Avicel® PH 102 showed similar results with respect to dissolution. Generally, an increase in agitation speed resulted in an faster rate of dissolution. These studies also showed that formulations containing 20% Pearlitol® (w/w) demonstrated improved dissolution as compared to formulations containing 10% Pearlitol®.

TABLE 8

| Ingredients | PLF-6 (a) Tablet | PLF-6 (b) Tablet | PLF-6 (c) Tablet | PLF-7 (d) Tablet | PLF-7 (e) Tablet |
|---|---|---|---|---|---|
| PLF-6 | | | | | |
| 3.0 g Testosterone | 240 mg | 240 mg | 240 mg | — | — |
| 2.7 g DSPC | | | | | |
| 0.3 g Cholesterol | | | | | |
| PLF-7 | | | | | |
| 1.2 g Testosterone | — | — | — | 360 mg | 240 mg |
| 1.080 g DSPC | | | | | |
| 0.12 g Cholesterol | | | | | |
| Pearlitol ® 200 SD | — | 130 mg | 65 mg | — | — |
| Avicel ® PH 101 | 388 mg | — | — | — | 388 mg |
| Avicel ® PH 102 | — | 259 mg | 323 mg | 268 mg | — |
| Explotab ®3 wt % | 19.50 mg | 19.50 mg | 19.50 mg | 19.50 mg | 19.50 mg |
| Mg stearate | 1.625 mg | 1.625 mg | 1.625 mg | 1.625 mg | 1.625 mg |

Example 8: Comparison of Dissolution of Formulations in the Form of Capsule, Tablet and Powder The dissolutions of a capsule form of PLF-2 and a tablet form of PLF-6 were compared to each other and to the dissolution of unformulated testosterone (T1-175). PLF-2 and PLF-6 were prepared as described in Examples 5 and 7, respectively, and further formulated by the external addition of excipients as reported in Table 9. Dissolution of formulations in the form of capsule, tablet were compared with that of pure drug in PBS (pH 6.80) with 1% (w/v) SLS. The addition of 1% (w/v) SLS showed complete drug release within 0.5 h. The in vitro release profiles are shown in FIG. 14. Formulations a, b, and c in Table 9 correlated with lines a, b, and c of FIG. 14.

TABLE 9

| Ingredients | a Capsule | b 650 mg tablet | c Pure Drug |
| --- | --- | --- | --- |
| Testosterone | — | — | 50 mg |
| PLF-2 | 100 mg | — | — |
| PLF-6 | — | 240 mg | — |
| Avicel® PH 101 | 200 mg | 388 mg | — |
| Explotab® 3 wt % | — | 19.50 mg | — |
| Magnesium stearate | — | 1.625 mg | — |

Example 9: Dissolution of Testosterone/Cholesterol DSPC Proliposomal Formulations with Avicel® PH 102 and Explotab® Disintegrant Capsule formulations PLF-9 (a-e) were prepared by the external addition of Avicel® PH 102 and Explotab® disintegrant, as reported in Table 10, including two formulations were prepared with a minimum amount of Avicel®, both with and without Explotab® disintegrant. Compositions of all the formulations described in this example are listed in Table 10. Dissolution of all these formulations was carried out using a type II apparatus with a capsule sinker in PBS (pH 6.80) medium that did not contain SLS. The objective of these studies was to determine whether the increase in ratio of Avicel® to testosterone would increase the solubility of testosterone from proliposomal formulations.

The in vitro release profiles of the formulations listed in Table 10 are shown in FIG. 15. Formulations with a base formulation:Avicel® ratio of 1:1 correlated to greater testosterone release. The other preparations that contained minimum amounts of Avicel® showed less testosterone release due to poor dispersion of the formulations. The compositions of PLF-9 and PLF-2 were the same, except the batch size for PLF-9 was scaled to 5 g, rather than the 3 g batch size of PLF-2.

TABLE 10

| Ingredients | PLF-9 (a) Vcaps® size '00' | PLF-9 (b) Vcaps® size '00' | PLF-9 (c) Vcaps® size '00' | PLF-9 (d) Vcaps® Plus size '0' | PLF-9 (e) Vcaps® Plus size '00' |
| --- | --- | --- | --- | --- | --- |
| PLF-9 | 120 mg | 120 mg | 120 mg | 240 mg | 240 mg |
| Avicel® PH 102 | 240 mg (1:2) | 60 mg (1:0.5) | 120 mg (1:1) | 40 mg (1:0.6) | 40 mg (1:0.6) |
| Explotab® | — | — | — | — | 8.5 mg |

Example 10: Dissolution of Testosterone/Cholesterol DSPC Proliposomal Formulations with Minimum Amounts of Avicel® PH102, and Explotab® Disintegrant in HPMC Size '0' Capsules HPMC size '0' capsule formulations PLF-11 (a and b) and PLF-12 (c and d) were prepared by the external addition of Avicel® PH 102 and Explotab® disintegrant, as reported in Table 11 to PLF-10, which was prepared according to the same protocol used to make PLF-2 as described in Example 2. All of these formulations contained minimum amounts of Avicel®, both with and without Explotab® disintegrant. The formulations in Table 11 were filled into Vcaps® Plus hypromellose (HPMC) capsules (Capsugel, Belgium Nev.) In vitro dissolution studies were carried out using a type II apparatus at 75 rpm. The dissolution media used was: a) PBS with 1% (w/v) SLS; b) PBS with 2% (w/v) SLS; c) PBS with 0.5% (w/v) SLS; and d) PBS with 1% (w/v) SLS. Media containing 1% and 2% (w/v) SLS showed complete drug release within 2 hours. The in vitro dissolution profiles of formulations (a-d) are shown in FIG. 16.

TABLE 11

| Ingredients | PLF-11 (a) Vcaps® Plus size '0' | PLF-11 (b) Vcaps® Plus size '0' | PLF-12 (c) Vcaps® Plus size '0' | PLF-12 (d) Vcaps® Plus size '0' |
| --- | --- | --- | --- | --- |
| PLF-10 | 240 mg | 240 mg | 240 mg | 240 mg |
| Avicel® PH 102 | 40 mg | 40 mg | 40 mg | 40 mg |
| Explotab® | — | — | 8.5 mg | 8.5 mg |

Example 11: Dissolution Behaviour of Testosterone/Cholesterol DSPC Proliposomal Formulations with Avicel® PH 102 in Size '0' Capsules The formulations PLF-14 (a) and PLF-15 (b), which are provided in Table 12 were prepared to determine the disintegration times of formulations filled in Vcaps (HPMC) size '0' and Vcaps® Plus (HPMC) size '0' capsules (Capsugel, Belgium Nev.). Formulation PLF-14 was also prepared to compare disintegration of Vcaps® versus Vcaps® Plus encapsulated formulations. Size '0' capsules were used to assess each capsule type. To perform the comparison study of Vcaps® and Vcaps Plus®, the capsules were filled with only Avicel®.

Formulation PLF-15, which contained the base testosterone, DSPC, and cholesterol components of PLF-13, Avicel®, and Explotab® in the amounts reported in Table 12, was used to compare dispersion times in the presence and absence of a sinker. A sinker is a basket like device made of a few turns of platinum wire that is used to prevent capsules from floating. These studies revealed that dispersion of capsules was more complete when a sinker was not used because the capsules were not confined within the sinker cage, and because the formulation were exposed to a larger surface area. See Table 12.

TABLE 12

| | (a) PLF-14 | | (b) PLF-15 | |
|---|---|---|---|---|
| Ingredients | Vcaps size '0' | Vcaps Plus size '0' | Vcaps size '0' Sinker used for dissolution | Vcaps size '0' Dissolved using a sinker |
| PLF-13 | | | | |
| Contains Testosterone, DSPC, and Cholesterol in ratios of 1:9:0.1 | — | — | 240 mg | 240 mg |
| Avicel ® PH 102 | 288 mg | | 40 mg | 40 mg |
| Explotab ® | — | | 8.5 mg | 8.5 mg |
| Disintegration | disintegrated in 8-11 min | disintegrated in 11-13 min | 10% of the capsule disperses in 30 min. | 90% of capsule gets dispersed in 30 min. DT & dispersion is fast |

Example 12: Dissolution of Testosterone/Cholesterol DSPC Proliposomal Formulations with Avicel® PH 102, Pros® Iv® SMCC 90, DCP, and Explotab® Disintegrant The base formulation, PLF-13, was further formulated to make PLF-16 (a), PLF-17 (b), PLF-18 (c), PLF-19 (d), PLF-20 (e), PLF-21 (f), and PLF (g) by the external addition of various amounts of different diluents Avicel® PH 102, Pros® Iv® SMCC 90 (Silicified Micro Crystalline Cellulose), and dibasic calcium phosphate (DCP) in combination with disintegrants. The formulations were prepared using the ingredients described in Table 13. PLF-13 contained testosterone, DSPC, and Cholesterol in a ratio of 1:0.9:0.1, which correlated with 60 mg, 54 mg, and 6 mg, respectively, per capsule.

PLF-13 was prepared as described in Example 2 for PLF-2, except that the preparation of PLF-13 was scaled to a 10 g batch size. The formulations in Table 13 were filled in Vcaps® size '0' HPMC capsules (Capsugel, Belgium Nev.). The in vitro dissolution was carried out using type II apparatus at 75 rpm in 1000 ml of PBS pH 6.80 with 0.5% SLS. No sinker was used in these studies. Formulations containing higher amounts of Avicel® PH 102 and DCP showed better release profiles (FIG. 17).

Example 13: Dissolution of Enteric Coated Capsules Containing Testosterone/Cholesterol DSPC Proliposomal Formulations with Avicel® PH 102, and Explotab® Disintegrant A base proliposomal formulation was prepared according to the description of the preparation of PLF-2 in Example 2, except that the batch size was scaled to 15 g. The base PLF-2 formulation was further formulated into PLF-25 by the external addition of excipients as reported in Table 14, and filled into Vcap® HPMC size '00' capsules (Capusulate, Belgium Nev.). Formulation PLF-24, which is also described in Table 14, served as a placebo control that did not contain testosterone. PLF-24 and PLF-25 were prepared as part of an effort to optimize the delayed release coating (e.g., an enteric coating) process for capsules of the invention.

After the PLF-24 and PLF-25 formulations were filled into capsules, the capsules were coated with an Eudragit® L 30D-55 polymer-based enteric coating composition. Coating of the capsules was accomplished by using a ProCepT® pan coating machine (Zelzate, Belgium) and a Caleva® mini coater air suspension coating machine (Dorset, UK). The Eudragit® L 30D-55 coating composition was used in accordance with its manufacturer's instructions and the coating process parameters are summarized in Tables 15 and 16. The capsules of the testosterone formulation were coated until the capsules experienced a 10.16% weight gain. The placebo formulation was coated until the capsules experienced an 11.06% weight gain. Based on these results, of the coating experiments, the percentage gain in weight for enteric coated capsules was fixed to 12%, which provided sufficient resistance to tablet dissolution in acidic pH. For the scale up formulations, Eudragit® L 100 55, which is available in powder form, was used for delayed release coating (e.g., an enteric coating).

The method used for in vitro dissolution was based on a method described in the United States Pharmacopeia (USP) 30, <711> Dissolution procedure for delayed release dosage forms (method B) that was modified by adding 0.5% (w/v) SLS for the dissolutions of delayed release dosage forms like enteric coated capsules. The method involves two stages of testing, the Acid stage and the Buffer stage. In the Acid stage, the dissolution was carried out in 1000 ml of 0.1N HCl, and maintained at 37±0.5° C. for 2 hours. After 2 hours, a sample aliquot was withdrawn to be used in the buffer stage. In the Buffer stage of testing, phosphate buffer that has been previously equilibrated to 37±0.5° C. was used. The acid was drained from the vessel and 1000 ml of pH 6.8 phosphate buffer, prepared by mixing 0.1 N HCl with 0.20 M tribasic sodium phosphate (3:1) and adjusting if necessary with 2 N HCL or 2 N sodium hydroxide, was added to the vessel. The apparatus ran for 4 hours, and sample aliquots

TABLE 13

| Ingredients | PLF-16 (a) | PLF-17 (b) | PLF-18 (c) | PLF-19 (d) | PLF-20 (e) | PLF-21 (f) | PLF-22 (g) |
|---|---|---|---|---|---|---|---|
| PLF-13 | 120 mg | 120 mg | 120 mg | 120 mg | 120 mg | 120 mg | 120 mg |
| DCP | — | — | — | 75 mg | — | — | 30 mg |
| Avicel ® PH 102 | 75 mg | 50 mg | — | — | 93.40 | — | — |
| Prosolv ® SMCC 90 | — | — | 75 mg | — | — | 30 mg | — |
| Explotab ® | 4.25 mg | 4.25 mg | 4.25 mg | 4.25 mg | 6.6 mg | 4.65 mg | 4.65 mg |
| Capsule type & size | Vcaps size '0' | Vcaps size '0' | Vcaps size '0' | Vcaps size '0' | Vcaps size '0' | Vcaps size '0' | Vcaps size '0' | were withdrawn at regular time intervals. The samples were analyzed using a suitable analytical technique. This modified method was used to test formulations PLF-24 and PLF-25. The dissolution medium used in the buffer stage was 1000 ml of phosphate buffer solution (PBS) pH 6.80 with 0.5% (w/v) SLS. PLF-24 and PLF-25 were intact in acidic pH for 2 hours. The capsules of active formulation showed complete drug release within 2 hours in PBS with 0.5% (w/v) SLS (FIG. 18).

A modified and validated HPLC assay method was used for the analysis of dissolution samples. HPLC analysis was carried out using mobile phase containing methanol:water (60:40 v/v). Separation was achieved on a C18; 150×4.6 mm (5 μm) (Ace) column. The mobile phase flow rate was set at 1.2 ml/min while the column temperature was maintained at 25° C. The total run time was 15 minutes with injection volume of 35 μl. The drug was detected using a UV detector at absorbance maxima of 246 nm. The retention time of testosterone was found to be 11.5 minutes. The method was able to resolve testosterone and all other excipients. The flow rate was kept high to reduce the run time for each sample to facilitate faste analysis.

TABLE 14

| Ingredients | (a) PLF-24 Placebo Enteric coated capsule | (b)PLF-25 Enteric coated capsule |
| --- | --- | --- |
| PLF-2 | No PLF-2 108 mg DSPC 12 mg cholesterol | 240 mg |
| Avicel ® PH 102 | 152 mg | 152 mg |
| Explotab ® | 12 mg | 12 mg |
| Total weight | 0.285 g | 0.405 g |
| Dosage form | Vcaps ® size '00' | Vcaps ® size '00' |
| % weight gain (w/w, increase/original total) of enteric coated capsules using Eudragit ® L 30D-55 | 11.06% | 10.16% |

TABLE 15

| Parameter | Value |
| --- | --- |
| Drum speed | 12 rpm |
| Atomizing air pressure | 1.5 bar |
| Pressure drop cabinet | 50.0 mBar |
| Inlet air temperature | 40° C. |
| Outlet air temperature | 50° C. |
| Dosing speed | 0.6 ml/min |
| Pump speed | 35 |

TABLE 16

| Parameter | Value |
| --- | --- |
| Agitation frequency | 25 Hz |
| Air inlet temperature | 40° C. |
| Pump Flow rate | 4 rpm |
| Air pressure | 1 bar |
| Fan speed | 16 m/sec |

Example 14: Dissolution of Enteric Coated Capsules Containing Testosterone/Cholesterol DSPC Proliposomal Formulations with Avicel® PH 102, Pros® Iv® SMCC 90/SMCC HD 90, and Explotab® Disintegrant Base formulations PLF-23 and PLF-28 were further formulated by the external addition of excipients, as described in Table 17, including the manual mixing of PLF-23 with two different grades of microcrystalline cellulose (Pros® Iv® HD 90 and Pros® Iv® SMCC 90) to make PLF-26 and PLF-27, respectively. PLF-23 and PLF-28 are compositionally identical to each other and to PLF-2, which is described in Example 2, and contains testosterone, DSPC, and cholesterol in the ratios of 1:0.9:0.1. The method used to prepare PLF-23 and PLF-28 was also the same method that was used to prepare PLF-2. PLF-28 was further formulated into PLF-29 by the external addition of excipients, excluding microcrystalline cellulose, as also described in Table 17.

PLF-26 and PLF-27 were filled into Vcaps® HPMC size '00' capsules (Capsulate, Belgium Nev.), and coated with the delayed release coating polymer, Eudragit® L 30D-55, according to the coating procedure described in Example 13.

PLF-29 was also filled into capsules, but unlike PLF-26 and PLF-27, it contained Avicel® PH 102, and remained uncoated. In order to determine the effect of curing on dissolution, PLF-29 capsules were cured by heating the capsules at 40 C in a hot air oven for two hours The method used for in vitro dissolution was based on a method described in the United States Pharmacopeia (USP) 30, <711> Dissolution procedure for delayed release dosage forms (method B that was modified by adding 0.5% (w/v) SLS for the dissolutions of delayed release dosage forms like enteric coated capsules. The method involves two stages of testing, the Acid stage and the Buffer stage. In the Acid stage, the dissolution was carried out in 1000 ml of 0.1N HCl, and maintained at 37±0.5° C. for 2 hours. After 2 hours, a sample aliquot was withdrawn to be used in the buffer stage. In the Buffer stage of testing, phosphate buffer that has been previously equilibrated to 37±0.5° C. was used. The acid was drained from the vessel and 1000 ml of pH 6.8 phosphate buffer, prepared by mixing 0.1 N HCl with 0.20 M tribasic sodium phosphate (3:1) and adjusting if necessary with 2 N HCL or 2 N sodium hydroxide, was added to the vessel. The apparatus ran for 4 hours, and sample aliquots were withdrawn at regular time intervals. The samples were analyzed using a suitable analytical technique. The dissolution medium used in the buffer stage was 1000 ml of phosphate buffer solution (PBS) pH 6.80 with 0.5% (w/v) SLS. Testosterone release from the collected samples was determined using a UV spectrophotometer at a wavelength of 246 nm. FIG. 19 shows the in vitro dissolution profiles of formulations (a-c).

TABLE 17

| Ingredients | PLF-26 (a) | PLF-27 (b) | PLF-29 (c) |
| --- | --- | --- | --- |
| PLF-23 | 240 mg PLF-23 | 240 mg PLF-23 | |
| PLF-28 | | | 240 mg PLF-28 |
| Avicel ® PH 102 | — | — | 152 mg |
| Prosolv ® SMCC 90 | — | 155 mg | — |
| Prosolv ® SMCC HD 90 | 155 mg | — | — |
| Explotab ® | 10 mg | 10 mg | 12 mg |
| Total capsule weight | 405 mg | 405 mg | 405 mg |
| Dosage form | Vcaps ® size '00' Enteric-coated | Vcaps ® size '00' Enteric-coated | Vcaps ® size '00' Heat cured |

In vitro testosterone dissolution studies were carried out using formulation PLF-28. The dissolution medium used for these studies was PBS (pH 6.80) with 0.5% (w/v) SLS, and the dissolution protocol followed is described in this Example, above. Samples were collected after 4 h of dissolution and used for particle size analysis by using a NICOMP (Santa Barbara, Calif.) model 370 sub micron particle size analyzer. These samples were not quantified for percent drug dissolution. Table 18 summarizes the results of the particle size analysis of the formulations as physical mixes and in matrix form after being subjected to dissolution.

TABLE 18

| Sample Details | Sample No. | Mean diameter of vesicles in nm based on: | | |
| --- | --- | --- | --- | --- |
| | | Number - weighted Gaussian distribution | Volume - weighted Gaussian distribution | Intensity - weighted Gaussian distribution |
| PLF-28 | 1 | 216.1 | 2061.2 | 932.0 |
| | 2 | 445.1 | 1369.1 | 929.9 |
| | 3 | 321.1 | 2873.5 | 1296.8 |
| Physical mix (Testosterone + DSPC + Cholesterol) | 1 | 366.0 | 1961.4 | 1041.9 |
| | 2 | 125.7 | 1999.9 | 736.3 |
| | 3 | 359.6 | 3437.4 | 1362.2 |

Example 15: Formulation and Evaluation of Testosterone Oral Delivery System

A. Preparation and Optimization of Proliposomal Testosterone Formulations

Testosterone and phospholipids (Table 19) were dissolved in ethanol and the solvent was evaporated using nitrogen gas. The dry powder was passed through #60 mesh screen to produce homogenous particle size distribution. Phospholipids employed in the study are from Inactive Ingredient Guide (FDA).

TABLE 19

| Formulation No. | Composition | Ratio | Amount (mg) |
| --- | --- | --- | --- |
| 1 | Test:DMPC | 1:1 | 200:200 |
| 2 | Test:DMPG | 1:1 | 200:200 |
| 3 | Test:DSPC | 1:1 | 200:200 |
| 4 | Test:DSPG | 1:1 | 200:200 |
| 5 | Test:(DMPC:DMPG) | 1:1 | 200:(100:100) |
| 6 | Test:(DSPC:DMPG) | 1:1 | 200:(100:100) |
| 7 | Test:(DMPC:Chol) | 1:(9:1) | 200:(180:20) |
| 8 | Test:(DMPC:DMPG:) | 1:(7:3) | 200:(140:60) |
| 9 | Test:(DSPC:Chol) | 1:(9:1) | 200:(180:20) |
| 10 | Test:(DSPC:DMPG:Chol) | 1:(4:4:2) | 200:(80:80:40) |
| 11 | Test:(DMPC:DMPG) | 1:(3:7) | 200:(60:140) |
| 12 | Test:(DSPC:DMPG) | 1:(7:3) | 200:(140:60) |
| 13 | Test:(DSPC:DMPG) | 1:(3:7) | 200:(60:140) |
| 14 | Test:(DSPC:Chol) | 1:(6:4) | 200:(120:80) |
| 15 | Test:(DSPC:DSPG) | 1:(1:1) | 200:(100:100) |

B. Transport Study
Caco-2 Cell Culture:

Monolayers of Caco-2 cells were prepared on 4 urn-pore polycarbonate Transwell® filters by the following method. Caco-2 cells were grown in T-75 flasks at 37° C. in an atmosphere of 5% $CO_2$ and 95% air using Dulbecco's Modified Eagle Medium (DMEM, pH 7.2) with the necessary growth supplements. The medium was changed at least once daily to 90% confluence. The cells were washed with Hank's Balanced Salt Solution (HBSS w/o $Ca^{+2}$, $Mg^{+2}$) and trypsinized with 0.25% trypsin in 1 mM EDTA for 5 min. at 37° C. The cells were resuspended in 10 ml of DMEM and processed to minimize aggregation of cells. Five ml of the cell suspension were withdrawn and seeded into 4-μm pore Transwell® inserts at a density of 7.5×10 cells/ml. Five ml of DMEM was added to the flask to make a 1:1 dilution of the cell suspension to DMEM, and the cells were re-seeded. The cells in the Transwell® inserts were grown for approximately five days and the resistance of the cells was measured every other day until resistance was greater than 100Ω.

C. In Vitro Transport Studies

Once the resistance of the cells reached greater than 100Ω the DMEM was carefully aspirated and replaced with 1.5 ml HBSS w/$Ca^{+2}$, $Mg^{+2}$ (which has been warmed in the 37° C. water bath) in the donor compartment and 2.5 ml in the receiver compartment using a micro pipette and allowed to equilibrate at room temperature for 30 minutes. Then the HBSS w/$Ca^{+2}$, $Mg^{+2}$ was carefully aspirated from the donor compartment and replaced with 0.5 mg/ml formulation which had been resuspended in HBSS w/$Ca^{+2}$, $Mg^{+2}$ (placed in 37° C. water bath for 30 minutes) prepared the previous day. Each formulation was tested in triplicates. The resistance was measured for each well (to ensure the cells stay intact) and 300 μl of sample was withdrawn from the receiver compartment and compensated with 300 μl of fresh HBSS w/$Ca^{+2}$, $Mg^{+2}$ for each time. Samples were withdrawn at times 5, 15, 30, 45, 60, 90, 120, 150, 180, 210, 240, 270, 300 minutes. The amount of testosterone transported was determined by analysis of 100 μl of the sample by HPLC. The experiments were performed in triplicate. Controls: 1. Unformulated testosterone control; 2. Testosterone proliposomal formulations Transport Study Results:

Transport of testosterone across Caco-2 cells after 5 hrs is shown in FIG. 20. The transport of testosterone was greater with all fifteen proliposomal formulations compared to control (processed and non-processed testosterone). Formulations prepared with DMPG and DSPC:Chol (9:1) exhibited the maximum transport of testosterone among the fifteen formulations evaluated in this study. The transport of testosterone was 2-fold greater than control (processed and non-processed testosterone). At the end of 5 hr sampling time, the transport had not reached plateau. This suggests the possibility of further enhancement of transport of testosterone beyond 5 hrs.

D. Conclusion

Addition of Cholesterol to DSPC facilitates improved transport of testosterone across the intestinal membrane. The improved transport of testosterone across the membrane was surprising positive result.

Example 16: Pharmacokinetics Studies

A clinical study was carried out that involved ten human subjects with hypogonadism. Medical examination was carried out prior to recruiting the patients for the study. The study was carried out in both fed and fasted conditions using a clinical study protocol that was approved by the Institutional Animal Care and Use Committee (IACUC). Informed consent was obtained from all the patients prior to the start of the study. Pharmacokinetics of testosterone after oral administration of the drug in two different doses (120 & 240 mg) was compiled. The mean plasma concentration of testosterone and its major metabolite Dihydro testosterone (DHT) under different treatment conditions is given in FIG. 21, 22. Absorption of testosterone was delayed in presence of food. Administration of higher dose of testosterone did not show any linear increase in the plasma concentration of testosterone. The peak plasma concentration ($C_{max}$) of testosterone was found after 5 hours ($C_{max}$) of administration of the drug for both strengths.

Example 17: Oral Dosage Form Containing Testosterone/Cholesterol DSPC Proliposomal Formulation An oral dosage form in the form of an enteric coated capsule was prepared on pilot scale for clinical study. The capsule contained, on a per capsule basis, a pharmaceutical composition having the ingredients listed in Table 20.

The oral dosage form was prepared by the following method using the components set out in Table 20. The method of preparing the oral dosage form is appropriate for the ranges indicated in Table 20 for each component provided by the table. The process involved dissolving testosterone in alcohol to get a clear solution. DSPC was added to the drug solution followed by addition of cholesterol to form a dispersion. The solvent was removed by evaporation using a rota evaporator under vacuum. Distillation until a dry mass was obtained. The dried lumps were then passed through sieve #60 and blended with microcrystalline cellulose and sodium starch glycolate. The formulation was filled into size '00' capsules using a semi automated capsule filling machine. The capsules were enteric coated using a methacrylic acid copolymer C.

TABLE 20

Components/Composition of Oral Dosage Form

| Core Components (capsule): | % wt range | Function |
|---|---|---|
| Testosterone USP | 12.5-60.0 | Active ingredient |
| Distearoylphosphatidyl-choline (DSPC) | 13.33-53.2 | Phospholipid |
| Cholesterol | 2.96-11.84 | Neutrolipid |
| Microcrystalline Cellulose NF (PH-102) | 9.87-37.74 | Filler/binder |
| Sodium Starch Glycolate NF | 1-5 | Disintegrant |
| Alcohol USP* | — | Solvent |
| Purified Water USP* | — | Solvent |

Example 18: Clinical Study of the Pharmacokinetics of Testosterone in Human Subjects with Hypogonadism A clinical study was carried out in 34 human subjects with hypogonadism to evaluate testosterone pharmacokinetics of over the course of their 15 day treatment periods with an oral dosage form of testosterone that contained the per-capsule amounts of the components provided in Table 21, and prepared according to the method described in Example 17. Subjects with 300 ng/dL serum testosterone were considered as hypogonadal. The inclusion criteria for all men to participate in the study was to have body mass index (BMI)<39 Kg/m$^2$, more than 18 years in age and the weight requirement was 55 Kg. All the subjects understood the purpose of the study and signed the informed consent form prior to participating in the study. The subject group was divided into two groups of 17 that were each administered twice-daily (i.e., morning and evening doses) dosages of either 120 mg or 240 mg (i.e., two 120 mg doses administered at the same time) of the formulated testosterone for 15 days. Plasma samples were taken on an hourly basis from the subjects after one full day and at 15 days after the dosing regimen began.

TABLE 21

| | Wt per capsule | Function |
|---|---|---|
| Core Components (capsule): | | |
| Testosterone USP | 120.0 mg | Active ingredient |
| Distearoylphosphatidyl-choline (DSPC) | 108.0 mg | Phospholipid |
| Cholesterol | 12.0 mg | Neutrolipid |
| Microcrystalline Cellulose NF (Avicel ® PH-102) | 152.85 mg | Filler/binder |
| Sodium Starch Glycolate NF (Explotab ®) | 12.15 mg | Disintegrant |
| Alcohol* | q.s | |
| Total | 405.0 mg | |
| HPMC capsules size '00' | 120.0 mg | |
| Enteric Coating composition (for capsule): | | |
| Methacrylic Acid Copolymer C. NF, | 39.5 mg | Enteric coating polymer |
| Triethyl Citrate NF | 3.95 mg | Plasticizer |
| Talc NF | 19.55 mg | Anti tacking agent |
| Purified water * | q.s. | Diluent |
| Total weight | 588.0 mg | |

FIG. 23 shows the separate averages of the combined hourly plasma testosterone concentrations from subjects on the 120 mg and 240 mg twice daily regimens over the course of the first and fifteenth days of treatment. As FIG. 23 indicates, twice-daily administration of the 240 mg dose of testosterone did not show any linear increase in the plasma concentration of testosterone than that of the twice-daily 120 mg regimen. On Day 1, the 120 mg and 240 mg dosing regimens each achieved average daily plasma testosterone concentrations of greater than 300 ng/dL in 71% of the subjects. On Day 15, the 120 mg and 240 mg dosing regimens achieved average daily plasma testosterone concentrations of greater than 300 ng/dL in 59% and 31% of the subjects, respectively. From day 1 to day 15 of the study, there were decreases in testosterone exposure for the subjects that were administered the 120 mg and 240 mg dosing regimens. The decrease associated with the 240 mg regimen was significant.

The average peak plasma concentration ($C_{max}$) of testosterone was reached four hours after the administration of either the 120 mg or 240 mg doses, at which point it was 500 ng/dL and greater than 500 ng/dL, respectively. See FIGS. 24 and 25.

Example 19: Evaluation of the Toxicity and Toxicokinetics of Proliposomal Dosage Forms The purpose of this study was to evaluate the toxicity and toxicokinetics of an oral dosage form of testosterone that contained the per-capsule amounts of the components provided in Table 21, and prepared according to the method described in Example 17. For these studies, a placebo, and three different doses of formulated testosterone were administered once daily to beagle dogs for a minimum of 90 consecutive days. More specifically, 16 male beagle dogs were assigned to four treatment groups in the toxicology portion of this study. Animals were dosed orally with capsules providing a target dose level of 0, 15, 75, or 150 mg/kg/day of formulated testosterone for 91 consecutive days. These dose levels are equivalent to o, 120 mg, 600 mg, and 1200 mg dosage forms. On day 92, animals were euthanized and subjected to a complete gross necropsy. Protocol-specified tissues, including testes, were collected and forwarded to Experimental Pathology Laboratories (EPL), Inc. Tissues from all groups were processed, embedded in paraffin, sectioned, and stained with hematoxylin and eosin (H&E). The resulting slides were forwarded to Brett Saladino, DVM, Diplomate ACVP of Calvert Laboratories for evaluation by light microscopy.

The only pathological findings that were attributed to the pharmacologic effects of exogenous testosterone on the testes and epididymides. Findings included hypospermatogenesis, increased multinucleate germ cells/syncytia, increased luminal spermatogenic cells, vacuolation/atrophy of Leydig cells, and tubular atrophy in the testes; and hypospermia and increased luminal debris in the epididymides. The findings were most striking in animals given 75 or 150 mg/ml/day.

Blood samples were also drawn at fixed time intervals and analyzed on days 1, 57 and 91 for 24 hour periods on each of those days. Blood samples were collected from all animals prior to treatment initiation and from study animals on days 29 and 92 via jugular vein puncture. See FIGS. 26, 27, and 28, respectively.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components. While an increase in plasma testosterone levels increased with increases in the amount of testosterone dosage, the increase was not proportional. Testosterone levels increased on day 57 compared to day 1. The levels increased with all three doses (120, 600 and 1200 mg). Testosterone levels decreased on day 91 compared to day 57. In case of 120 mg dose the testosterone level was lower than day 1.

What is claimed is:

1. A proliposomal powder dispersion, consisting essentially of (a) testosterone undecanoate, (b) cholesterol, and (c) at least one phospholipid, wherein (a) and (b) are present in a weight ratio (a):(b) ranging from 1.0:0.05 to 1.0:0.30 and (a), (b) and (c) are present in a weight ratio of (a):((b)+(c)) ranging from 1.0:1.0 and 1.0:2.5.

2. A proliposomal powder dispersion of claim 1, wherein the phospholipid is selected from distearoyl phosphatidylcholine, dipalmitoyl phosphatidylcholine, dimyristoyl phosphatidylcholine, egg phosphatidylcholine, soy phosphatidylcholine, dimyristyl phosphatidyl glycerol sodium, 1,2-dimyristoyl-phosphatidic acid, dipalmitoylphosphatidylglycerol, dipalmitoyl phosphate, 1,2-distearoyl-sn-glycero-3-phospho-rac-glycerol, 1,2-distearoyl-sn-glycero-3-phosphatidic acid, phosphatidylserine and sphingomyelin, or a combination thereof.

3. A proliposomal powder dispersion of claim 2 wherein the phospholipid is distearoyl phosphatidylcholine.

4. A pharmaceutical composition comprising a proliposomal powder dispersion of claim 1 and at least one pharmaceutically acceptable excipient.

5. An oral dosage form comprising the pharmaceutical composition of claim 4, wherein the oral dosage form is a tablet or capsule, and wherein the tablet or capsule is coated with a delayed release coating.

6. An oral dosage form comprising the pharmaceutical compositions of claim 5, wherein the oral dosage form is a tablet or capsule, and wherein the tablet or capsule is coated with an enteric coating.

7. An oral dosage form, comprising a proliposomal powder dispersion of claim 1 and at least one pharmaceutically acceptable excipient, wherein the testosterone undecanoate is present in an amount ranging from 50 to 260 mg and having a fasting pharmacokinetic profile of a mean plasma concentration of testosterone ranging from 300 to 950 ng/dL of testosterone at five hours after ingestion.

8. An oral dosage form of claim 7, wherein the oral dosage form is a capsule, and wherein the capsule is coated with a delayed release coating.

9. A proliposomal powder dispersion of claim 1, wherein: the phospholipid is selected from distearoyl phosphatidylcholine, dipalmitoyl phosphatidylcholine, dimyristoyl phosphatidylcholine, egg phosphatidylcholine, soy phosphatidylcholine, dimyristyl phosphatidyl glycerol sodium, 1,2-dimyristoyl-phosphatidic acid, dipalmitoylphosphatidylglycerol, dipalmitoyl phosphate, 1,2-distearoyl-sn-glycero-3-phospho-rac-glycerol, 1,2-distearoyl-sn-glycero-3-phosphatidic acid, phosphatidylserine and sphingomyelin, or a combination thereof; (a) and (b) are present in a weight ratio (a):(b) ranging from 1.0:0.08 to 1.0:to 0.12; and (a), (b) and (c) are present in a weight ratio of (a):((b)+(c)) ranging from 1.0:1.0 to 1.0:1.2.

10. A proliposomal powder dispersion of claim 9 wherein the phospholipid is distearoyl phosphatidylcholine.

11. A pharmaceutical composition comprising a proliposomal powder dispersion of claim 9 and at least one pharmaceutically acceptable excipient.

12. A method of treating an individual in need of testosterone therapy comprising administering to said individual a therapeutically effective amount of the proliposomal powder dispersion of claim 9.

13. A proliposomal powder dispersion of claim 1, wherein the dispersion is admixed with microcrystalline cellulose, and wherein the dispersion and the microcrystalline cellulose are present in a weight ratio ranging from about 1:0.5 to about 1:2.

14. An oral dosage form of claim 13, wherein the dispersion is admixed with microcrystalline cellulose, and wherein the dispersion and the microcrystalline cellulose are present in a weight ratio ranging from about 1:0.5 to about 1:2.

15. A proliposomal powder dispersion according to claim 14, wherein the dispersion and the microcrystalline cellulose are present in a weight ratio ranging from about 1:0.5 to about 1:1.

16. An oral dosage form according to claim 15, wherein the dispersion and the microcrystalline cellulose are present in a weight ratio ranging from about 1:0.5 to about 1:1, and wherein the native testosterone is present in an amount ranging from 50 to 260 mg and having a fasting pharmacokinetic profile of a mean plasma concentration of testosterone ranging from 300 to 950 ng/dL of testosterone at five hours after ingestion.

17. An oral dosage form of claim 14, having a fasting pharmacokinetic profile of a mean plasma concentration of testosterone ranging from 350 to 950 ng/dL of testosterone at five hours after ingestion.

* * * * *